United States Patent
Miller et al.

(10) Patent No.: US 8,734,786 B2
(45) Date of Patent: May 27, 2014

(54) USE OF ECDI-FIXED CELL TOLERANCE AS A METHOD FOR PREVENTING ALLOGRAFT REJECTION

(75) Inventors: Stephen D. Miller, Oak Park, IL (US); Xunrong Luo, Chicago, IL (US)

(73) Assignee: Northwestern University, Evanston, IL (US)

( * ) Notice: Subject to any disclaimer, the term of this patent is extended or adjusted under 35 U.S.C. 154(b) by 551 days.

(21) Appl. No.: 12/883,763

(22) Filed: Sep. 16, 2010

(65) Prior Publication Data
US 2011/0064709 A1   Mar. 17, 2011

Related U.S. Application Data

(60) Provisional application No. 61/242,917, filed on Sep. 16, 2009.

(51) Int. Cl.
 A01N 63/00  (2006.01)
 A01N 65/00  (2009.01)
 C12N 5/00  (2006.01)
 C12N 5/02  (2006.01)

(52) U.S. Cl.
 USPC ........................................ 424/93.7; 435/325

(58) Field of Classification Search
 None
 See application file for complete search history.

(56) References Cited

PUBLICATIONS

Miller et al., "Antigen-specific tolerance strategies for the prevention and treatment of autoimmune disease," Nat Rev Immunol, 7:665-677 (2007).
Mohanakumar et al., "A significant role for histocompatibility in human islet transplantation," Transplantation, 82:180-187 (2006).
Moreau et al., "Transient increase in symptoms associated with cytokine release in patients with multiple sclerosis," Brain, 119:225-237 (1996).
Muthukumar et al., "Messenger RNA for FOXP3 in the urine of renal-allograft recipients," N Engl J Med., 353:2342-2351(2005).
Nakanishi et al., "CD8(+) T lymphocyte mobilization to virus-infected tissue requires CD4(+) T-cell help," Nature, 462:510-513 (2009).
Nakayama et al., "Prime role for an insulin epitope in the development of type 1 diabetes in NOD mice," Nature, 435:220-223 (2005).
Nir et al., "Recovery from diabetes in mice by beta cell regeneration," J Clin Invest, 117:2553-2561 (2007).
Ochando et al., "Alloantigen-presenting plasmacytoid dendritic cells mediate tolerance to vascularized grafts," Nat Immunol., 7:652-662 (2006).
Perruche et al., "CD3-specific antibody-induced immune tolerance involves transforming growth factor-beta from phagocytes digesting apoptotic T cells," Nat Med., 14:528-535 (2008).
Peterson et al., "Split tolerance of Th1 and Th2 cells in tolerance to Theiler's murine encephalomyelitis virus," Eur J Immunol, 23:46-55 (1993).
Podojil et al., "Therapeutic blockade of T-cell antigen receptor signal transduction and costimulation in autoimmune disease," Adv Exp Med Biol., 640:234-251(2008).
Quezada et al., "Tumor-reactive CD4(+) T cells develop cytotoxic activity and eradicate large established melanoma after transfer into lymphopenic hosts," J. Exp. Med., 207:637-650 (2010).
Ranheim et al., "Activated T cells induce expression of B7/BB1 on normal or leukemic B cells through a CD40-dependent signal," J Exp Med, 177:925-935 (1993).
Ridge et al., "A conditioned dendritic cell can be a temporal bridge between a CD4+ T-helper and a T-killer cell," Nature, 393:474-478 (1998).
Roopenian et al., "The immunogenomics of minor histocompatibility antigens," Immunol. Rev., 190:86-94 (2002).
Ryan, et al. "Five-year follow-up after clinical islet transplantation," Diabetes 54:2060-2069 (2005).
Scandling , et al. "Tolerance and chimerism after renal and hematopoietic-cell transplantation," N Engl J Med 358:362-368 (2008).
Schneider et al., "Development of suppressor lymphocytes during acute rejection of rat cardiac allografts and preservation of suppression by anti-IL-2-receptor monoclonal antibody," Transplantation, 42:191-196 (1986).
Shapiro, et al. "International trial of the Edmonton protocol for islet transplantation.," N Engl J Med 355:1318-1330 (2006).
Shepherd et al., "Disruption of CD154:CD40 blocks generation of allograft immunity without affecting APC activation," J Immunol., 163:2470-2477 (1999).
Simpson et al., "The male-specific histocompatibility antigen, H-Y: a history of transplantation, immune response genes, sex determination and expression cloning," Annu Rev Immunol., 15:39-61(1997).
Smith et al., "Differential induction of IgE-mediated anaphylaxis after soluble vs. cell-bound tolerogenic peptide therapy of autoimmune encephalomyelitis," PNAS, 102:9595-9600 (2005).
Sotomayor et al., "Conversion of tumor-specific CD4+ T-cell tolerance to T-cell priming through in vivo ligation of CD40," Nat Med, 5:780-787 (1999).
Sun et al. "CD4+ T cells are required for the maintenance, not programming, of memory CD8+ T cells after acute infection," Nat Immunol, 5:927-933 (2004).
Tan et al., "Regulation of the effector stages of experimental autoimmune encephalomyelitis via neuroantigen-specific tolerance induction. II. Fine specificity of effector T cell inhibition," J Immunol 148:2748-2755 (1992).
Teshima et al., "Acute graft-versus-host disease does not require alloantigen expression on host epithelium," Nat. Med., 8:575-581 (2002).
Turley et al., "Peripheral tolerance induction using ethylenecarbodiimide-fixed APCs uses both direct and indirect mechanisms of antigen presentation for prevention of experimental autoimmune encephalomyelitis," J Immunol 178:2212-2220 (2007).
Valujskikh et al., "Cross-primed CD8(+) T cells mediate graft rejection via a distinct effector pathway," Nat. Immunol., 3:844-851(2002).

(Continued)

*Primary Examiner* — Debbie K Ware

(74) *Attorney, Agent, or Firm* — Casimir Jones S.C.

(57) ABSTRACT

The present invention provides methods, systems, and compositions for inducing donor-specific tolerance. In particular, the present invention provides methods of administering ECDI-treated cells before, during, and/or after administration of donor transplant cells or a donor allograft in order to induce tolerance for the cells and/or allograft in a recipient.

13 Claims, 16 Drawing Sheets

(56) References Cited

PUBLICATIONS

Vanderlugt, et al. "Pathologic role and temporal appearance of newly emerging autoepitopes in relapsing experimental autoimmune encephalomyelitis," J Immunol 164:670-678 (2000).

VanderVegt et al., "Induction of long-term H-Y-specific tolerance in female mice given male lymphoid cells while transiently depleted of CD4+ or CD8+ T cells," J. Exp. Med., 177:1587-1592 (1993).

Williams et al., "Interleukin-2 signals during priming are required for secondary expansion of CD8+ memory T cells," Nature, 441:890-893 (2006).

Williams et al., "Effector and memory CTL differentiation," Annu Rev Immunol, 25:171-192 (2007).

Xia et al., "Ex vivo-expanded natural CD4+CD25+ regulatory T cells synergize with host T-cell depletion to promote long-term survival of allografts," Am J Transplant, 8:298-306 (2008).

Zelenika et al., "Rejection of H-Y disparate skin grafts by monospecific CD4+ Th1 and Th2 cells: no requirement for CD8+ T cells or B cells," J. Immunol., 161:1868-1874 (1998).

Zijlstra et al., "Skin graft rejection by beta 2-microglobulin-deficient mice," J. Exp. Med., 175:885-893 (1992).

Amrani et al., "CD154-dependent priming of diabetogenic CD4(+) T cells dissociated from activation of antigen-presenting cells," 2002, Immunity, 16:719-732.

Banchereau et al., "Functional CD40 antigen on B cells, dendritic cells and fibroblasts," Adv Exp Med Biol, 378:79-83 (1995).

Bennett et al., "Induction of a CD8+ cytotoxic T lymphocyte response by cross-priming requires cognate CD4+ T cell help," J Exp Med, 186:65-70 (1997).

Benveniste et al., "Role of macrophages/microglia in multiple sclerosis and experimental allergic encephalomyelitis," J. Mol. Med., 75:165-173 (1997).

Bluestone, "Regulatory T-cell therapy: Is it ready for the clinic?," Nat Rev Immunol, 5:343-349 (2005).

Boehm et al., "Cellular responses to interferon-gamma," Annu. Rev. Immunol., 15:749-795 (1997).

Buller et al., "Induction of cytotoxic T-cell responses in vivo in the absence of CD4 helper cells," Nature, 328:77-79 (1987).

Bushell et al., "Transplantation tolerance induced by antigen pretreatment and depleting anti-CD4 antibody depends on CD4+ T cell regulation during the induction phase of the response," 1995, Eur J Immunol., 25:2643-2649.

Busker et al., "Induction of allograft tolerance to the H-Y antigen in adult C57BL/6 mice: differential effects on delayed-type hypersensitivity and cytolytic T-lymphocyte activity," 1990, Cell Immunol, 125:225-234.

Campbell et al., "High risk of sensitization after failed islet transplantation," Am J Transplant, 7:2311-2317(2007).

Castellino et al., "Cooperation between CD4+ and CD8+ T cells: when, where, and how," Annu Rev Immunol, 24:519-540 (2006).

Chai et al., "Transplantation tolerance induced by intranasal administration of HY peptides," Blood, 103:3951-3959 (2004).

Cook et al., "Spontaneous renal allograft acceptance associated with "regulatory" dendritic cells and IDO," J Immunol., 180:3103-3112 (2008).

Croft, M., "The role of TNF superfamily members in T-cell function and diseases," Nat. Rev. Immunol., 9:271-285 (2009).

Eagar et al., "The role of CTLA-4 in induction and maintenance of peripheral T cell tolerance," Eur. J. Immunol., 32:972-981(2002).

Eagar et al., "CTLA-4 regulates expansion and differentiation of Th1 cells following induction of peripheral T cell tolerance," J Immunol 172:7442-7450 (2004).

Elgueta et al., "Molecular mechanism and function of CD40/CD40L engagement in the immune system," Immunol. Rev, 229:152-172 (2009).

Elliott et al., "Ethylcarbodiimide as an agent for induction of specific transplant tolerance," Transplantation 58:966-968 (1994).

Ferguson et al., "Uptake of apoptotic antigen-coupled cells by lymphoid dendritic cells and cross-priming of CD8(+) T cells produce active immune unresponsiveness," J. Immunol., 168:5589-5595 (2002).

Fife et al. "Insulin-induced remission in new-onset NOD mice is maintained by the PD-1-PD-L1 pathway," J Exp Med 203:2737-2747 (2006).

Fischbein et al., "CD40 signaling replaces CD4+ lymphocytes and its blocking prevents chronic rejection of heart transplants," J Immunol, 165:7316-7322 (2000).

French et al., "CD40 antibody evokes a cytotoxic T-cell response that eradicates lymphoma and bypasses T-cell help," Nat Med, 5:548-553 (1999).

Getts et al., "Differential outcome of tolerance induction in naive versus activated Theiler's virus epitope-specific CD8+ cytotoxic T cells," J. Virol, 81:6584-6593 (2007).

Gonsette, "Compared benefit of approved and experimental immunosuppressive therapeutic approaches in multiple sclerosis," Expert Opin Pharmacother., 8:1103-1116 (2007).

Greenwald et al., "The B7 family revisited," Annu Rev. Immunol., 23:515-548 (2005).

Gurung et al., "Activation-induced CD154 expression abrogates tolerance induced by apoptotic cells," J. Immunol., 183:6114-6123 (2009).

Hahn et al., "Mechanism and biological significance of CD4-mediated cytotoxicity," Immunol. Rev., 146:57-79 (1995).

Heppner et al., "Experimental autoimmune encephalomyelitis repressed by microglial paralysis," Nat. Med., 11:146-152 (2005).

Hyder et al., "Effect of the immunosuppressive regime of Edmonton protocol on the long-term in vitro insulin secretion from islets of two different species and age categories," Toxicol in Vitro, 19:541-546 (2005).

James et al., "HY peptides modulate transplantation responses to skin allografts," Int Immunol, 14:1333-1342 (2002).

Janeway et al., "Innate immune recognition," Annu Rev Immunol, 20:197-216 (2002).

Jenkins et al., "Allogeneic non-T spleen cells restore the responsiveness of normal T cell clones stimulated with antigen and chemically modified antigen-presenting cells.," J Immunol., 140:3324-3330 (1988).

Jenkins et al., "Antigen presentation by chemically modified splenocytes induces antigen-specific T cell unresponsiveness in vitro and in vivo," J Exp Med, 165:302-319 (1987).

Joffre et al., "Prevention of acute and chronic allograft rejection with CD4+CD25+Foxp3+ regulatory T lymphocytes," Nat Med., 14:88-92 (2008).

Johnson et al., "Selected Toll-like receptor ligands and viruses promote helper-independent cytotoxic T cell priming by upregulating CD40L on dendritic cells," Immunity, 30:218-227 (2009).

Kaneko et al., "Alloantigen presentation by ethylcarbodiimide-treated dendritic cells induces T cell hyporesponsiveness, and prolongs organ graft survival," Clin Immunol 108:190-198 (2003).

Kawai T, et al. "HLA-mismatched renal transplantation without maintenance immunosuppression," N Engl J Med 358:353-361 (2008).

Kazama et al., "Induction of immunological tolerance by apoptotic cells requires caspase-dependent oxidation of high-mobility group box-1 protein," Immunity, 29:21-32 (2008).

Kennedy, et al. "Inhibition of murine relapsing experimental autoimmune encephalomyelitis by immune tolerance to proteolipid protein and its encephalitogenic peptides," J Immunol 144:909-915 (1990).

Koenen et al., "Antigen-specific regulatory T-cell subsets in transplantation tolerance regulatory T-cell subset quality reduces the need for quantity," Hum Immunol., 67:665-675 (2006).

Kohm et al., "Cutting edge: CD4+CD25+ regulatory T cells suppress antigen-specific autoreactive immune responses and central nervous system inflammation during active experimental autoimmune encephalomyelitis," J Immunol, 169:4712-4716 (2002).

Kohm et al., "Treatment with nonmitogenic anti-CD3 monoclonal antibody induces CD4+ T cell unresponsiveness and functional reversal of established experimental autoimmune encephalomyelitis," J. Immunol., 174:4525-4534 (2005).

Lechler et al. "Organ transplantation—how much of the promise has been realized?," Nat Med, 11:605-613 (2005).

Lin et al., "Dominant transplantation tolerance impairs CD8+ T cell function but not expansion," Nat. Immunol., 3:1208-1213 (2002).

(56) References Cited

OTHER PUBLICATIONS

Lineberry et al., "Cutting edge: The transmembrane E3 ligase GRAIL ubiquitinates the costimulatory molecule CD40 ligand during the induction of T cell anergy," J. Immunol., 181:1622-1626 (2008).

Lobo et al., "Development of anti-human leukocyte antigen class 1 antibodies following allogeneic islet cell transplantation," Transplant Proc., 37:3438-3440 (2005).

Long et al., "Regulatory T cells—a journey from rodents to the clinic," Front Biosci, 12:4042-4049 (2007).

Luo et al., "Dendritic cells with TGF-beta1 differentiate naive CD4+CD25-T cells into islet-protective Foxp3+ regulatory T cells," PNAS, 104:2821-2826 (2007).

Luo et al., "ECDI-fixed allogeneic splenocytes induce donor-specific tolerance for long-term survival of islet transplants via two distinct mechanisms," PNAS, 105:14527-14532 (2008).

Miller et al., "The induction of cell-mediated immunity and tolerance with protein antigens coupled to syngeneic lymphoid cells," J Exp Med, 149:758-773 (1979).

USE OF ECDI-FIXED CELL TOLERANCE AS A METHOD FOR PREVENTING ALLOGRAFT REJECTION

CROSS REFERENCE INFORMATION

The present invention claims the benefit of U.S. Provisional Patent Application Ser. No. 61/242,917, filed Sep. 16, 2009, which is incorporated herein by reference in its entirety.

FIELD OF THE INVENTION

The present invention provides methods, systems, and compositions for inducing donor-specific tolerance. In particular, the present invention provides methods of administering ECDI-treated cells before, during, and/or after administration of donor transplant cells or a donor allograft in order to induce tolerance for the cells and/or allograft in a recipient.

BACKGROUND

Allogeneic islet cell transplantation is a promising therapy for patients who have autoimmune diabetes (Shapiro A M, et al. (2006) *N Engl J Med* 355:1318-1330.; Ryan E A, et al. (2005) *Diabetes* 54:2060-2069.; herein incorporated by reference in their entireties). However, as in solid-organ transplantation, robust donor-specific allogeneic responses (Mohanakumar T, et al. (2006) *Transplantation* 82:180-187.; Campbell P M, et al. (2007) *Am J Transplant* 7:2311-2317.; herein incorporated by reference in their entireties) necessitate life-long immunosuppression that increases the risk for fatal opportunistic infections. In addition, the currently used immunosuppression regimen has intrinsic β-cell toxicity (Nir T, Melton D A, Dor Y (2007) *J Clin Invest* 117:2553-2561.; Hyder A, Laue C, Schrezenmeir J (2005) *Toxicol In Vitro* 19:541-546.; herein incorporated by reference in their entireties). Therefore, a means of establishing donor-specific tolerance to obviate the need for immunosuppression is highly desirable for therapeutic cell or allograft transplantation.

Strategies for inducing alloantigen-specific tolerance include mixed hematopoietic chimerism, costimulation blockade, peripheral T-cell depletion, and induction and expansion of regulatory T cells (Tregs) (Lechler R I, Sykes M, Thomson A W, Turka L A (2005) *Nat Med* 11:605-613.; herein incorporated by reference in its entirety). Most regimens require myeloablation/cytoreduction and/or blocking antibodies targeting various T-cell signaling components, and these antibodies have significant toxicities. Using Tregs is less toxic, but the main challenge is to obtain sufficient numbers of alloantigen-specific Tregs (Long E T, Wood K J (2007) *Front Biosci* 12:4042-4049.; Luo X, et al. (2007) *Proc Natl Acad Sci USA* 104:2821-2826.; herein incorporated by reference in their entireties).

Previous studies have shown that i.v. injection of antigen-pulsed splenic antigen-presenting cells (APCs) chemically fixed with 1-ethyl-3-(3'-dimethylaminopropyl)-carbodiimide (ECDI) is a powerful and safe method to induce antigen-specific T-cell tolerance in vivo (Kennedy M K, et al. (1990) *J Immunol* 144:909-915.; Tan L J, Kennedy M K, Miller S D (1992) *J Immunol* 148:2748-2755.; herein incorporated by reference in their entireties). Specifically, myelin peptide-coupled, ECDI-fixed syngeneic APCs could effectively ablate induction and progression of experimental autoimmune encephalomyelitis (EAE), a murine Th1/17-mediated model of multiple sclerosis (Vanderlugt C L, et al. (2000) *J Immunol* 164:670-678.; herein incorporated by reference in its entirety). Recent work using this tolerance method has defined the importance of cross-tolerance via host APCs and the role of specific Tregs (Kohm A P, Carpentier P A, Anger H A, Miller S D (2002) *J Immunol* 169:4712-4716.; Kohm A P, et al. (2005) *J Immunol* 174:4525-4534.; Miller S D, Turley D M, Podojil J R (2007) *Nat Rev Immunol* 7:665-677.; herein incorporated by reference in their entireties). This protocol also is effective in preventing and treating autoimmune diabetes in nonobese diabetic (NOD) mice (Fife B T, et al. (2006) *J Exp Med* 203:2737-2747.; herein incorporated by reference in its entirety).

What is needed are more effective methods of inducing donor cell tolerance in a recipient receiving donor cells or an allograft.

SUMMARY OF THE INVENTION

The present invention provides methods, systems, and compositions for inducing donor-specific tolerance. For example, the present invention provides methods of administering donor ECDI-treated cells both before and after (or during) administration of donor transplant cells or a donor allograft in order to induce donor-specific tolerance in a recipient.

In certain embodiments, the present invention provides methods of cell or allograft transplantation comprising: a) administering a first type of cells to a recipient prior to step b), wherein the first type of cells are from a donor and are ECDI-treated cells; b) administering a second type of cells or an allograft to the recipient, wherein the second type of cells and the allograft are from the donor; and c) administering the first type of cells to the recipient during or after step b).

In particular embodiments, the administering in step c) is after the administering a second type of cell or an allograft to the recipient in step b) (e.g., 5 minutes after . . . 1 hour after . . . 12 hours after . . . 24 hours after . . . 3 days after . . . 10 days after . . . etc.). In certain embodiments, the administering in step c) is performed 1-96 hours after step b) (e.g., 1-96, 6-36, or 12-24 hours after step b). In other embodiments, the administering in step c) is performed 12-36 hours after step b).

In some embodiments, the administering in step a) is performed 1-28 or 1-14 days prior to step b) (e.g., 1 . . . 5 . . . 10 . . . 15 . . . 20 . . . or 28 days prior to step b)). In certain embodiments, the administering in step a) is performed 4-10 days prior to step b).

Any combination of times mentioned above for ECDI-treated cell administration before and after step b) may be employed (e.g., 3 days before and 1 day after, or 7 days before and 1 day after, or 1 day before and 6 days after, etc.).

The present invention is not limited by the first type of cells as all useful types of cells are contemplated. In further embodiments, the first type of cells comprise leukocytes. In other embodiments, the first type of cells comprise splenocytes. In further embodiments, the second type of cells comprise parenchymal cells from an organ. In some embodiments, the second type of cells comprise islet cells. In some embodiments, the allograft comprises at least part of an organ selected from the group consisting of: kidney, pancreas, heart, liver, large instestine, small intestine, lung, and stomach.

In other embodiments, the administering in steps a) and c) induces donor-specific tolerance to the second type of cells or the allograft in the recipient. In further embodiments, the donor-specific tolerance to the second type of cells or the allograft lasts for at least 50 days (e.g., at least 50 . . . 75 . . . 100 . . . 150 . . . 250 . . . or for the life of the recipient) in the recipient in the absence of an additional immunosuppressive regime. In some embodiments, the recipient has not received any additional immunosuppressive agents for at least 50 days (e.g., at least 50 ... 75 ... 100 ... 150 ... 250 ... or for the life of the recipient) from step b), and the second type of cells and/or the allograft are not rejected for the at least 50 days (e.g., at least 50 ... 75 ... 100 ... 150 ... 250 ... or for the life of the recipient). In some embodiments, ECDI-treated cells comprise cells which were contacted with ECDI in the presence of one or more antigens and/or epitopes. In some embodiments, antigens and/or epitopes comprise all or a portion of a peptide, protein, or glycoprotein. In some embodiments, antigens and/or epitopes comprise all or a portion of CD4.

In particular embodiments, the present invention provides compositions comprising: ECDI-treated splenocytes and a physiologically tolerable buffer. In other embodiments, the compositions contain between $1 \times 10^7$ and $1 \times 10^{10}$ of the ECDI-treated cells. In further embodiments, the compositions are free or substantially free of red blood cells. In further embodiments, the compositions are free or substantially free of non-ECDI-treated spenocyte cells.

In certain embodiments, the present invention provides systems comprising: a) a syringe vial; and b) a composition comprising: ECDI-treated splenocytes and a physiologically tolerable buffer, wherein the composition is located in the syringe vial.

In some embodiments, the present invention provides a system comprising: (a) ECDI-treated cells from a donor; and (b) an allograft of transplant cells from said donor. In some embodiments, the ECDI-treated cells are selected from the group consisting of: splenocytes, islet cells, and red blood cells.

DESCRIPTION OF THE FIGURES

FIG. 1A shows a time line of the treatment protocols, and FIG. 1B shows graft survival. Day 0 indicates the day of islet transplantation. ECDI-treated BALB/c cells vs. control, P=0.0036; ECDI-treated SJL cells vs. control, P=0.2178; untreated BALB/c cells vs. control, P<0.0001. FIG. 1C shows three alternative treatment protocols that do not provide ECDI-treated cells both before and after cell transplantation, and FIG. 1D shows the poor survival rates with these alternative treatment protocols.

FIG. 2 shows protected grafts at day 14 (A) and day 70 (B) after transplantation that were stained with H&E, anti-insulin, CD4, +Foxp3, and CD8. Graphs are representatives of at least four sectioned and stained grafts of each group. Magnification×100. Asterisks indicate intact islets.

FIG. 3A shows long-term tolerized B6 recipients (60-90 days after the first transplantation) were nephrectomized to remove the first graft and were transplanted with a second same-donor (BALB/c, n=3) or third-party (SJL, n=3) graft. Day 0 indicates the day of the second islet graft transplantation. FIG. 3B shows graft histology of the second islet graft. Upper panels: a protected same-donor BALB/c graft; Lower panels: a rejected third-party SJL graft. Magnification×100.

FIG. 4A shows DTH responses. P=0.0018, rejecting vs. tolerized recipients. FIG. 4B shows specific anti-donor antibodies that were measured for IgG1, IgG2a, IgG2b, and IgG3. The top two rows of histograms are results from two control (rejected) recipients. The bottom two rows of histograms are results from two long-term tolerized recipients. Data are representative of two individual experiments. Shaded histogram indicates syngeneic cells. (C) Mixed lymphocyte reaction and IFN-γ production. Thy1.2$^+$ T cells from the spleens and peripheral lymph nodes from control and tolerized recipients were used. P values are indicated in the graphs. Data are representative of three separate experiments.

FIG. 5A shows PC61 treatment at the time of tolerance induction abrogated graft protection in recipients receiving ECDI-treated donor cell infusions. Day 0 indicates the day of islet transplantation. The dotted line indicates the blood glucose level of 250 mg/dl, which was used to diagnose graft rejection. FIG. 5B shows quantification of the CD4$^+$CD25$^+$Foxp3$^+$ T-cell population in peripheral lymphoid organs from rejecting, tolerized, or PC61-treated recipients on day 15 after transplantation. Data were expressed as the percentage of total CD4$^+$ T cells that were Foxp3$^+$ cells. dLNs=draining lymph nodes; pLNs=peripheral lymph nodes. *Rejecting vs. tolerized, P=0.0076; **, PC61-treated vs. tolerized, P=0.0013; #PC61-treated vs. tolerized, P=0.0086; &PC61-treated vs. tolerized, P=0.026. FIG. 5C shows anti-donor IFN-γ production by rejecting, tolerized, or PC61-treated recipients. *Rejecting vs. tolerized, P=0.0009; **rejecting vs. PC61-treated, P=0.0012. FIG. 5D shows PC61 treatment in long-term tolerized recipients (n=3). Treatment was given on day 118 and day 120 after islet transplantation as indicated by the arrows. Blood glucose levels were followed for an additional 50 days after PC61 treatment. FIG. 5E shows anti-TGF-β treatment at the time of tolerance induction abrogated graft protection in recipients receiving infusions of ECDI-treated donor cell.

FIG. 6A shows islet graft survival in PD-L1$^{-/-}$ recipients with or without ECDI treatment. Day 0 indicates the day of islet transplantation. FIG. 6B shows anti-donor IFN-γ production by PD-L1$^{-/-}$ vs. wild-type recipients receiving ECDI treatment. *, PD-L1$^{-/-}$ ECDI-treated vs. wild-type ECDI-treated; P=0.0005. FIG. 6C shows quantification of the CD4$^+$CD25$^+$Foxp3$^+$ T-cell population in peripheral lymphoid organs from PD-L1$^{-/-}$ vs. wild-type recipients receiving ECDI-treated cells.

FIG. 7A shows naive B6 females treated i.v. with syngeneic female SPs ECDI-linked to the CD4 epitope (Dby) or the CD8 Hya epitopes (Uty and Smcy) or not tolerized on days −7 and 0 relative to engraftment with male tail skin grafts. Untreated control mice were included as a baseline for rejection time. Graft survival was monitored visually for 100 d. Male skin graft survival was significantly prolonged in female recipients treated with female Dby-SP (filled circles) compared with both untreated (open circles) and Uty/Smcy-SP treated (filled triangles) female recipients. FIG. 6B shows DTH responses of female B6 mice to ear challenge with 10 μg soluble Dby determined at 10, 20, and 60 d posttransplantation in naive, untreated and Dby-SP-treated female B6 mice.

Ear swelling responses in naive B6 mice served as the baseline. Ear swelling responses in Dby-SP-treated mice were significantly less than those in nontolerized controls. FIGS. 6C and D show in vitro recall responses of splenic T cells from untreated and Dby-SP-tolerized mice determined 10 d posttransplantation upon stimulation with anti-CD3 (clone 2C11, positive control), $OVA_{323-339}$ (negative control), and Dby peptides by [$^3$H]thymidine incorporation (C) and IFN-γ secretion (D). Proliferative and IFN-γ responses were significantly suppressed in Dby-SP-tolerized animals upon challenge with either the CD4 (Dby) or CD8 (Uty and Smcy) Hya epitopes. Proliferative responses to Dby could be restored to control levels by the addition of 25 U/ml exogenous IL-2. FIG. 7E shows antigen specificity of the induction and effector stages of the regulatory effect tested by treating female B6 mice i.v. with syngeneic female splenocytes ECDI-coupled with either $OVA_{323-339}$ or the Dby peptide at days −7 and 0 relative to engraftment with both male B6 skin and female skin from a C57BL/10 donor. Neither Dby-SP (open circles) nor $OVA_{323-339}$-SP (open triangles) treatment significantly prolonged B10 skin graft survival. However, Dby-SPs (closed circles), but not $OVA_{323-339}$-SPs (closed triangles), significantly protected male B6 grafts from rejection.

FIG. 8A shows live, single CD8+ cells. FIG. 8B-M shows CD44 expression on Uty-specific CD8+ T cells in spleens (B-D) and draining lymph nodes (H-J), and Smcy-specific CD8+ T cells in spleens (E-G) and draining lymph nodes (K-M) of naive, nontolerized (No Rx), and i.v. Dby-SP-tolerized female B6 mice receiving B6 male tail skin grafts 14 d previously are shown. The total number of tetramer-positive events is listed on each dot plot. Percentages of activated (CD44+) graft-specific CD8 cells, which appear in the top region of the tetramer-positive box, are also listed.

In FIGS. 9A-D, whole male splenocytes (specific) versus female splenocytes (reference) were used. In FIGS. 9E-H, female splenocytes were pulsed with a combination of the Hya Uty and Smcy peptides (specific) or TMEV VP2 (reference). In FIGS. 9I and 9K, female splenocytes were pulsed with a combination of the Hya Uty, Smcy, and Dby peptides (specific) or TMEV VP2 and $OVA_{323-339}$ (reference). White bars on the graphs (D, H, L) represent calculated lysis in nontreated graft recipients, black bars represent lysis observed in Dby-SP-treated recipients, and gray bars represent lysis observed in unmanipulated naive female controls. In vivo cytolytic responses in Dby-SP-tolerized mice were significantly lower than those in nontolerized controls.

In FIGS. 10A-F, B6 $OVA_{323-339}$-specific OT-II TCR transgenic mice were untreated (naive) (A, D) or injected i.v. with 10$^8$ $OVA_{323-339}$-SPs (B, E) or 10$^8$ $MBP_{84-104}$-SPs (C, F). Seven days later, splenocytes from these animals were harvested, stained, and analyzed for surface expression of CD154 immediately upon explant and again at 6 h following in vitro restimulation with 5 μM $OVA_{323-339}$. Maximal CD154 expression was observed at 6 h postculture. FIG. 10G is an FMO (fluorescence minus one) control.

In FIG. 11A, five to seven untreated (No Rx) and Dby-SP-tolerized female B6 mice received male tail skin grafts on day 0. Twenty-four hours later, separate groups of treated mice were injected i.p. with 100 μg IgG2a isotype control Ab or the agonistic anti-CD40 mAb, FGK45.5. Graft survival was monitored by visual inspection for 100 d. The prolonged survival of male skin grafts observed in Dby-SP-tolerized recipients treated with isotype control Ab was completely reversed by FGK45.5 treatment. In FIGS. 11B and C, Ten days posttransplantation and Ab treatment, recall responses of splenic T cells from the various treatment groups to in vitro stimulation with the Dby peptide were determined by [$^3$H]thymidine incorporation (B) and IFN-γ secretion (C). Suppressed proliferative and IFN-γ responses in the Dby-SP-tolerized animals were significantly reversed by treatment with FGK45.5.

In FIGS. 12A-F, ten days posttransplantation, spleens from these treated mice were analyzed for the frequency of activated (CD44$^+$) Hya Uty (A-C) and Smcy epitope-specific CD8$^+$ T cells (D-F) using MHC class I tetramers. In FIG. 12G, the total numbers of activated Hya-specific CD8$^+$ T cells are plotted. Similar results were observed upon analysis of lymph node CD8$^+$ T cells. In FIGS. 12H and I, the in vitro IFN-γ recall response of splenocytes from the various treatment groups to recall stimulation with the Hya CD4 and CD8 epitopes was determined (H), as was the in vivo lytic activity of two targets pulsed with a combination of the Hya Uty and Smcy CD8 epitopes (target) or TMEV VP2 (reference) (I). The IFN-γ response was restored to stimulation with the CD4 Dby epitope, but neither IFN-γ production nor the lytic function of CD8 T cells specific for the Uty or Smcy epitopes was restored by CD40 ligation.

In FIGS. 13A-J, B6 female mice received female (A, B) and male (C-J) skin grafts following treatment with Uty/Smcy-SPs (C, D), nothing (E, F), Dby-SPs and rIgG2a (G, H), or Dby-SPs and FGK45.5 (I, J). Ten days after engraftment, histologic sections were prepared from graft-containing tail areas and stained for CD4 (B, D, F, H, J) or CD8 (A, C, E, G, I). Grafts from mice displaying rejection (i.e., Uty/Smcy-SP-treated, Dby-SP- and FGK45.5-treated, and untreated groups) contain variable amounts of CD8 infiltrate and considerable CD4 infiltrate. Grafts that are retained (female control grafts and male grafts on Dby-SP and rIgG2a-treated females) contain very few infiltrating T cells. Original magnification is ×20.

In FIGS. 14A-D, CD86 expression was upregulated on the cells of graft recipients treated with FGK45.5 (D) but not those treated with isotype control (C) nor on naive control animals (B). E and F, Enumeration and phenotyping revealed that the majority of CD86 expressers are B cells (E) and DCs (F).

DEFINITIONS

Figure 1:
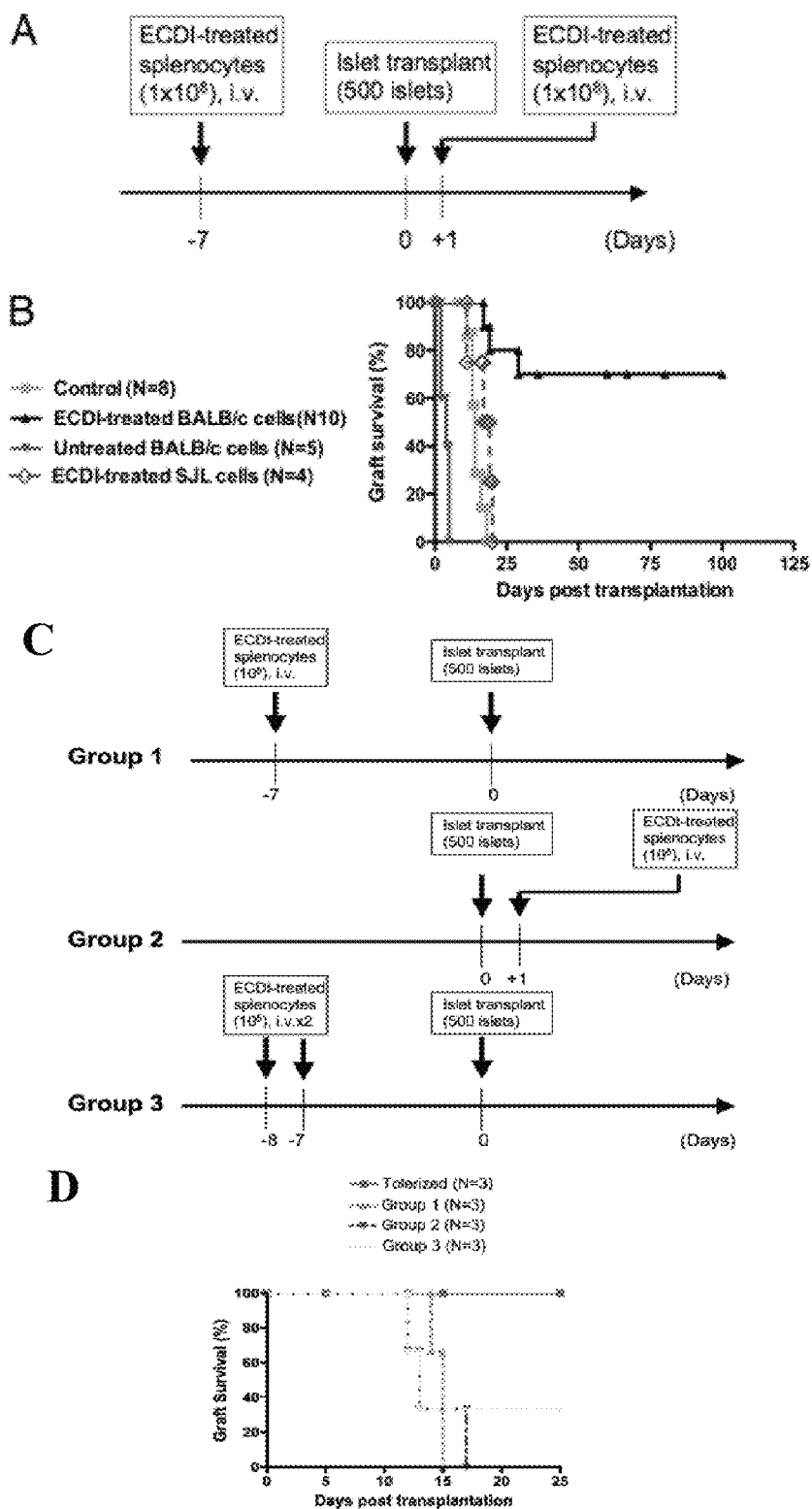
FIG. 1 shows results from Example 1 which shows that repeated infusions of ECDI-treated donor splenocytes induce significant graft protection in allogeneic islet cell transplantation.

As used herein, the term "ECDI-treatment" refers to the process of exposing cells and/or other materials (e.g. epitopes, antigens, lysed cells) to ethylene carbodiimide (aka 1-ethyl-3-(3-dimethylaminopropyl) carbodiimide, ECDI, EDC, EDAC, and/or EDCI). "ECDI treatment" of cells is commonly performed in the presence of one or more antigens and/or epitopes.

As used herein, the terms "ECDI-treated cell" refers to any cells (e.g. splenocyctes), which have been exposed to ECDI according to suitable methods described herein or understood by those of skill in the art. In some embodiments, "ECDI-treated cells" are coupled to one or more antigens and/or epitopes as a result of ECDI-treatment.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

As used herein, the term "epitope" refers to any determinant (e.g. a polypeptide determinant), capable of specific binding to an immunoglobulin or T-cell receptor. In some embodiments, an "epitope" is one or more portions of an antigenic protein or polypeptide. In certain embodiments, "epitope" determinants include chemically active surface groupings of molecules such as amino acids, sugar side chains, phosphoryl groups, or sulfonyl groups, and, in certain embodiments, may have specific three-dimensional structural characteristics, and/or specific charge characteristics. An epitope is a region of an antigen that is bound by an antibody.

As used herein, the terms "antigen-coupled cell" and "epitope-coupled cell" refer to a cell which has been modified by the attachment of one or more antigens to the cell surface. An "antigen-coupled cell" or "epitope-coupled cell" does not refer to a cell presenting it native set of antigens and/or epitopes. In some embodiments, "antigen-coupled cells" and/or "epitope-coupled cells" are produced by ECDI-treatment of cells in the presence of one or more antigens and/or epitopes, according to methods described herein and/or by other suitable methods understood by one of skill in the art.

As used herein, the term "subject" refers to any organism involved in any aspect (e.g. donor, recipient, antigen-provider, etc.) of one or more methods, compositions, or systems of the present invention. In some embodiments, a subject is a human, non-human primate, mammal, rodent, mouse, rat, canine, feline, porcine, equine, bovine, fish, bird, etc. In some embodiments, the term "patient" is used interchangeably to describe a human "subject."

As used herein, the term "3$^{rd}$ party" refers to any subject other than the donor and recipient of a transplant, allograft, allotransplant, etc. A "3$^{rd}$ party" is typically of the same species, sex, family, or comprises some set of similar characteristics to either the donor, recipient, or both.

DETAILED DESCRIPTION

The present invention provides methods, systems, and compositions for inducing donor-specific tolerance. In particular, the present invention provides methods of administering ECDI-treated cells before, during, and/or after administration of donor transplant cells or a donor allograft in order to induce tolerance for the cells and/or allograft in a recipient.

A major challenge for human allogeneic islet transplantation is the development of effective methods to induce donor-specific tolerance to obviate the need for life-long immunosuppression that is toxic to the insulin-producing β cells and detrimental to the host. The present invention addresses this need as it provides an efficient donor-specific tolerance therapy that utilizes infusions of ethylene carbodiimide (ECDI)-treated donor cells (e.g., splenic antigen-presenting cells) that results in long-term or indefinite survival of allogeneic donor cells (e.g., islet grafts) in the absence of immunosuppression. While the present invention is not limited to any mechanism, and an understanding of the mechanism is not necessary to practice the invention, certain results were identified during development of embodiments of the invention that relate to a proposed mechanism. For example, work conducted during the development of the present invention indicated that induction of tolerance is likely dependent on synergistic effects between an intact programmed death 1 receptor—programmed death ligand 1 signaling pathway and $CD4^+CD25^+Foxp3^+$ regulatory T cells.

As described in Example 1 below, it was found that i.v. infusion of ECDI-treated donor splenocytes induced long-term or indefinite donor-specific tolerance in allogeneic islet cell transplantation. While the present invention is not limited to any mechanism, and an understanding of the mechanism is not necessary to practice the invention, certain results were identified during development of embodiments of the invention that relate to a proposed mechanism. For example, the antigens of interest are mainly donor MHC class I and II molecules that are an integral surface component of donor lymphocytes, and ECDI treatment presumably interferes with costimulatory signals leading to tolerance induction to the membrane-bound allogeneic MHC antigens (Turley D M, Miller S D (2007) *J Immunol* 178:2212-2220.; Jenkins M K, Ashwell J D, Schwartz R H (1988) *J Immunol* 140:3324-3330.; herein incorporated by reference in their entireties). Two previous studies examined the efficacy of ECDI-treated donor dendritic cells or whole splenocytes in full MHC-mismatched heart and skin transplant models (Elliott C, Wang K, Miller S, Melvold R (1994) *Transplantation* 58:966-968.; Kaneko K, Morelli A E, Wang Z, Thomson A W (2003) *Clin Immunol* 108:190-198.; herein incorporated by reference in their entireties). Transient graft protection was observed, but long-term donor specific tolerance was not achieved. Embodiments of the present invention, unlike the previous work, are able to provide for long-term donor specific tolerance. While the present invention is not limited to any particular mechanism, it is believed that the methods of the present invention induce a programmed death-1 (PD-1)/programmed death ligand 1 (PD-L1)—dependent down-regulation of effector T-cell (Teff) activity and, independently, up-regulation of Tregs, which act synergistically to establish tolerance.

As described in Example 2 below, in humans and certain strains of laboratory mice, male tissue is recognized as non-self and destroyed by the female immune system via recognition of histocompatibility Y chromosome Ag (Hya). Male tissue destruction is thought to be accomplished by cytotoxic lymphocytes (CTLs) in a helper-dependent manner. Experiments conducted during development of embodiments of the present invention demonstrate that graft protection induced with the immunodominant Hya-encoded CD4 epitope (Dby) attached to female splenic leukocytes (Dby-SPs) with the chemical cross-linker ethylenecarbodiimide significantly, and often indefinitely, prolongs the survival of male skin graft transplants in an antigen-specific manner. In contrast, treatments with the Hya CD8 epitopes (Uty-/Smcy-SPs) failed to prolong graft survival. Dby-SP-tolerized CD4$^+$ T cells fail to proliferate, secrete IFN-γ, or effectively prime a CD8 response in recipients of male grafts. Antigen-coupled splenocyte treatment is associated with defective CD40-CD40L interactions as demonstrated by the observation that CD4 cells from treated animals exhibit a defect in CD40L upregulation following in vitro antigen challenge. Furthermore, treatment with an agonistic anti-CD40 antibody at the time of transplantation abrogates protection from graft rejection. Interestingly, anti-CD40 treatment completely restores the function of Dby-specific CD4 cells but not Uty- or Smcy-specific CD8 cells.

In some embodiments, the present invention provides methods of administering ECDI-treated donor cells both before and after (and/or during) administration of donor transplant cells or a donor allograft in order to induce donor-specific tolerance in a recipient. In some embodiments, the present invention provides administering antigen-coupled cells (e.g. ECDI-induced coupling) before, during, and/or after administration of donor transplant cells or a donor allograft in order to induce tolerance for the cells and/or allograft in a recipient. In some embodiments, the present invention provides administering epitope-coupled cells (e.g. ECDI-induced coupling) before, during, and/or after administration of donor transplant cells or a donor allograft in order to induce tolerance for the cells and/or allograft in a recipient.

In some embodiments, donor cells (e.g. splenocytes) are treated with ECDI in the presence of suitable antigen(s) and/or epitope(s) (e.g. CD4). In some embodiments, ECDI-treatment results in coupling of antigen(s) and/or epitope(s) to donor cells. In some embodiments, the ECDI-treated cells (e.g. epitope-coupled cells) are administered to a subject prior to transplantation of donor cells and/or tissue to the recipient. In some embodiments, the ECDI-treated cells (e.g. epitope-coupled cells) are co-administered to a subject during transplantation of donor cells and/or tissue to the recipient. In some embodiments, the ECDI-treated cells (e.g. epitope-coupled cells) are administered to a subject following transplantation of donor cells and/or tissue to the recipient. In some embodiments, administering ECDI-treated cells (e.g. epitope-coupled cells) to a allotransplant recipient before, during, and/or after transplantation results in increased tolerance (e.g. initial tolerance, long-term tolerance, total acceptance, etc.) of the transplanted material (e.g. of cells and/or tissue). In some embodiments, administering ECDI-treated cells (e.g. epitope-coupled cells) to a allotransplant recipient results in tolerance of transplanted materials without additional immunosupression or anti-rejection therapies.

In some embodiments, ECDI-treated cells, antigen-coupled cells, and/or epitope-coupled cells comprise donor cells (e.g. cells from the cell and/or allograft donor). In some embodiments, ECDI-treated cells, antigen-coupled cells, and/or epitope-coupled cells comprise recipient cells (e.g. cells from the cell and/or allograft recipient). In some embodiments, ECDI-treated cells, antigen-coupled cells, and/or epitope-coupled cells comprise 3$^{rd}$ party cells (e.g. cells from neither the donor nor recipient). In some embodiments, 3$^{rd}$ party cells are from a subject of the same species, sex, family, etc. as the recipient and/or donor. In some embodiments ECDI-treatment of cells is performed in the presence of one or more antigens and/or epitopes (e.g. donor epitopes, CD4, etc.). In some embodiments, ECDI-treatment of cells results in coupling of antigens and/or epitopes to cells undergoing ECDI-treatment. In some embodiments, antigens and/or epitopes comprise recipient antigens and/or epitopes. In some embodiments, antigens and/or epitopes comprise donor antigens and/or epitopes. In some embodiments, antigens and/or epitopes comprise 3$^{rd}$ party antigens and/or epitopes (e.g. synthetic, recombinant, or from a related (e.g. same species, sex family, etc.) subject). In some embodiments, donor cells and recipient antigens and/or epitopes are exposed to ECDI-treatment. In some embodiments, recipient antigens and/or epitopes are coupled to donor cells (e.g. ECDI-induced coupling). In some embodiments, recipient cells and donor antigens and/or epitopes are exposed to ECDI-treatment. In some embodiments, donor antigens and/or epitopes are coupled to recipient cells (e.g. ECDI-induced coupling). In some embodiments, 3$^{rd}$ party cells and donor antigens and/or epitopes are exposed to ECDI-treatment. In some embodiments, donor antigens and/or epitopes are coupled to 3$^{rd}$ party cells (e.g. ECDI-induced coupling). In some embodiments, 3$^{rd}$ party cells and recipient antigens and/or epitopes are exposed to ECDI-treatment. In some embodiments, recipient antigens and/or epitopes are coupled to 3$^{rd}$ party cells (e.g. ECDI-induced coupling).

In some embodiments, cells comprise any suitable cell type, for example, blood cells, (e.g. leukocytes (e.g. splenic leukocytes), erythrocytes, etc.), muscle cells, dendritic cells, neuronal cells, epithelial cells, etc. In some embodiments, cells administered ECDI-treatment comprise leukocytes (e.g. splenic leukocytes). In some embodiments, cells administered ECDI-treatment comprise splenocytes. In some embodiments, cells administered ECDI-treatment comprise donor cells, recipient cells, and/or 3$^{rd}$ party cells. In some embodiments, cells administered ECDI-treatment comprise cells from the same species, sex, cell type, family, etc. as the donor and or recipient.

In some embodiments antigens and/or epitopes which find use in embodiments of the present invention induce tolerance of donor cells and/or donor allografts in a recipient receiving such cells and/or tissues. In some embodiments antigens and/or epitopes comprise donor antigens and/or epitopes, recipient antigens and/or epitopes, and/or 3$^{rd}$ party antigens and/or epitopes. In some embodiments antigens and/or epitopes comprise all or a portion of a protein, peptide, and/or glycoprotein. In some embodiments antigens and/or epitopes comprise all or a portion of a glycoprotein (e.g. cluster of differentiation). In some embodiments antigens and/or epitopes comprise all or a portion of a cluster of differentiation (e.g. CD1, CD2, CD3, CD4, CD5, CD6, CD7, CD8, CD9, CD10, CD11a, CD11b, CD11c, CD12w, CD13, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD40, CD41, CD42, CD43, CD44, CD45, CD46, CD47, CD48, CD49b, CD49c, CD53, CD54, CD55, CD56, CD58, CD59, CD61, CD62E, CD62L, CD62P, CD63, CD68, CD69, CD71, CD72, CD74, CD80, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD1154, CD156, CD158, CD163, CD166, CD168, CD184, CDw186, CD209, CD202a, CD235a, CD271, CD303, CD304, and CD326). In some embodiments, antigens and/or epitopes comprise all or a portion of CD4. In some embodiments, antigens and/or epitopes comprise all or a portion of any protein, peptide, glycopeptides, carbohydrate, nucleic acid, etc. known by those of skill in the art to function in pathways involved in immunity to, and/or tolerance of, foreign substances, composition, cells, tissues, etc.

In some embodiments, the present invention provides methods, systems, and compositions for inducing tolerance of transplant donor cells and or tissue. In some embodiments, the present invention provides recipient tolerance of donor cells and/or tissues prior to allotransplantation (e.g. cells, tissues, organs), allograft, cell transplantation, solid-organ transplantation, etc. In some embodiments, the present invention provides methods, systems, and compositions for inducing tolerance of transplant donor cells and or tissue in anterior cruciate ligament (ACL) repair, Joint reconstruction in the knee and ankle, meniscal replacement, shoulder repair, spinal fusion, skin transplants, corneal transplants, heart transplants, heart valves, lung transplantation, liver transplants, kidney transplants, bone marrow transplants, bone allograft, ligament or tendon allograft, stem cell transplant, islet cell transplant, allogenic islet grafts, etc. In some embodiments, the present invention provides methods, systems, and compositions for inducing tolerance of allogenic islet grafts. In some embodiments, the present invention provides methods, systems, and compositions for inducing tolerance of cross-sex (e.g. male to female, or female to male allogenic transplants (e.g. cell, tissue, or organ).

In some embodiments, the tolerance inducing systems, methods, and compositions of the present invention are provided in conjunction with other anit-rejection and/or immunosuppresion techniques known to those of skill in the art (e.g. transient cell depletion, antibody-mediated blockade of costimulatory signals, peri-transplantation application of immunosuppressive drugs, etc.). In some embodiments, the present invention eliminates the need for anti-rejection and/or immunosuppresion therapy (e.g. transient cell depletion, antibody-mediated blockade of costimulatory signals, peri-transplantation application of immunosuppressive drugs, etc.) following transplantation. In some embodiments, the present invention reduces the necessity and/or duration of anti-rejection and/or immunosuppresion therapy following transplantation.

In some embodiments, the present invention provides ECDI-treatment of cells. In some embodiments, cells (e.g. spleen cells) are treated with ECDI. In some embodiments, cells (e.g. spleen cells) are treated with ECDI according to previously described procedures (Miller et al. 1979. *J. Exp. Med.* 149: 758-773; herein incorporated by reference in its entirety). In some embodiments, the present invention comprises alterations of the above ECDI-treatment procedure (e.g. buffer, duration, temperature, concentration, reagents, cell types, source of antigens and/or epitopes, etc.) which are within the understanding of one of skill in the art. In some embodiments, cells are treated with ECDI in the presence of one or more antigens and/or epitopes (e.g. CD4, lysed erythrocytes, etc.). In some embodiments, ECDI-treatment of cells in the presence of one or more antigens and/or epitopes (e.g. CD4, lysed erythrocytes, etc.) results in coupling of antigens and or epitopes to the cell surface (e.g. via ECDI).

In some embodiments, ECDI-treated cells, antigen-coupled cells, and/or epitope-coupled cells are administered to a subject to induce tolerance of cell and/or tissue allografts. In some embodiments, allograft transplant comprises the transplantation of donor cells and/or tissues to a recipient subject, wherein the donor and recipient are different subjects, but from the same species. In some embodiments, ECDI-treated donor cells are administered to the recipient before, during, and/or after allotrasplantation. In some embodiments, donor cells are ECDI-treated in the presence of one or more antigen and/or eptiopes (e.g. CD4). In some embodiments, donor cells at coupled to general epitopes and/or antigens from said recipient by ECDI-treatment. In some embodiments, donor cells at coupled to specific epitopes and/or antigens (e.g. CD4) from said recipient by ECDI-treatment. In some embodiments, donor cells at coupled to specific epitopes and/or antigens (e.g. CD4) from a $3^{rd}$ party source (e.g. synthetic antigen, recombinant antigen, antigen from another subject, etc.) by ECDI-treatment.

In some embodiments, epitope-coupled (e.g. CD4-coupled) donor cells are administered to the recipient before, during, and/or after allotrasplantation. In some embodiments, administration of ECDI-treated and/or epitope-coupled donor cells to an allograft recipient before, during, and/or after allotransplantation induces tolerance for the donor cells, tissue, and/or organ being allotrasplanted. In some embodiments, tolerance of donor cells and/or tissues lasts for a period of time following administration of ECDI-treated and/or epitope-coupled donor cells (e.g. 1 hour . . . 2 hours . . . 4 hours . . . 12 hours . . . 1 day . . . 2 days . . . 1 week . . . 1 month . . . 6 months . . . 1 year . . . indefinitely).

In some embodiments, systems, methods, and compositions of the present invention provide tolerance of donor cells and/or tissues through one or more pathways and or mechanism, although the present invention is not limited to any particular mechanism of action and an understanding of the mechanism of action is not necessary to practice the present invention. In some embodiments, the present invention suppresses recognition of donor alloantigens. In some embodiments, the present invention suppresses T cell response to donor cells and/or tissues. In some embodiments, the present invention suppresses B cell response to donor cells and/or tissues.

In some embodiments, the present invention provides treatment of cells and/or antigens with ECDI. In some embodiments, the present invention provides treatment with one or more ECDI derivatives, functionalized ECDI, and/or substituted ECDI. In some embodiments, the present invention provides treatment with suitable carbodiimide derivatives, e.g., ECDI, N,N'-diisopropylcarbodiimide (DIC), N,N'-dicyclohexylcarbodiimide (DCC), and other carbodiimide derivatives understood by those in the art.

EXAMPLES

The following Examples are presented in order to provide certain exemplary embodiments of the present invention and are not intended to limit the scope thereof.

Example 1

ECDI-Treated Donor Splenocyte Infusions Induce Indefinite Donor-Specific Tolerance in Allogeneic Donor Cell Transplantation This example describes the use of ECDI treated donor splenocytes to induce donor specific tolerance to islet cell transplantation in a recipient.

Materials and Methods

Mice.

Eight- to 20-week-old male BALB/c ($H2^d$) and C57BL/6 ($H2^b$) mice and male PD-L1$^{-/-}$ mice on C57BL/6 background were used in experiments conducted during development of embodiments of the present invention. All mice were housed under specific pathogen-free conditions at Northwestern University (NU). Protocols were approved by the NU Institutional Animal Care and Use Committee.

Antibodies.

APC-conjugated anti-CD25 (PC61) and FITC-conjugated anti-CD25 (7D4), anti-CD4 (GK1.5), and PE-conjugated anti-CD4 (L3T4; GK1.5) were from BD Biosciences. PE-conjugated anti-mouse Foxp3 (FJK-16a) was from eBiosciences. PC61 antibody (rIgG1, given at 0.5 mg per mouse every other day for two doses) was from Bio Express. Anti-TGF-β antibody (rIgG1, given at 0.3 mg per mouse every other day for six doses) was from R&D.

Coupled Cell Tolerance.

Tolerance was induced by i.v. injection of ECDI-treated splenocytes (Miller et al. (1979) *J Exp Med* 149:758-773.; herein incorporated by reference in its entirety). Spleens were processed into single-cell suspensions. Red blood cells were lysed, and splenocytes were incubated with ECDI (Calbiochem, 150 mg/ml per $3.2 \times 10^8$ cells) on ice for 1 hour with agitation followed by washing; $10^8$ ECDI-treated splenocytes in 200 ml of PBS were used for each injection.

Diabetes Experiments.

Mice were treated with streptozotocin (Sigma Aldrich) at 170 mg/kg. Two consecutive glucose readings (1 day apart) >250 mg/dl were used to diagnose diabetes (Long E T, Wood K J (2007) *Front Biosci* 12:4042-4049.; herein incorporated by reference in its entirety). Approximately 500 islets were implanted under the kidney capsule of recipient mice. Graft rejection was determined by two consecutive blood glucose readings >250 mg/dl.

Antibody Measurement.

Ear thickness was measured at baseline with a Mitutoyo engineer's micrometer (Schlesinger's Tool). A total of $10^7$ irradiated BALB/c and control B6 splenocytes in 10 μl PBS were injected into either ear, and swelling was determined 24 hours later. Results were reported as the difference in mean swelling between the donor- and recipient-challenged ears in units of $10^{-4}$ inches. For mixed lymphocyte reactions, a total of $10^5$ cells per well of Thy1.2$^+$ T cells from B6 islet recipients were cultured in a 96-well plate with irradiated splenocytes from donor BALB/c mice at a 5:1 APC/T-cell ratio. Cultures were pulsed with 1 μCi per well of [$^3$H]thymidine (PerkinElmer) during the last 18 hours of a 5-day culture. Culture supernatants were analyzed with the Liquichip Mouse 10-cytokine assay kit (Qiagen) and confirmed with ELISA for IFN-γ (BD Biosciences). For donor-specific antibody measurement, blood was collected with heparin, lysed, and incubated with splenocytes from BALB/c mice for 1 hour. Cells then were washed and stained with PE-conjugated anti-B220 mAb and with FITC-conjugated anti-IgM, anti-IgG1, anti-IgG2a, anti-IgG2b, and anti-IgG3 mantibodies (BD PharMingen). Syngeneic cells were used as negative control.

Immunohistochemistry and Immunofluorescence.

Snap-frozen sections of islet grafts were blocked with peroxidase (Dako). Anti-insulin rabbit IgG antibody (Dako) was used to detect islets. For detection of CD4$^+$Foxp3$^+$ T cells, sections were blocked with anti-CD16/32 and incubated with anti-Foxp3 mAb (rIgG2a clone FJK-16; eBiosciences). CD4 and CD8 staining were accomplished by anti-CD4-FITC mAb (rIgG2a clone RM4-5; eBiosciences) and biotinylated anti-mouse CD8a; BD PharMingen). Antibody binding was visualized using a secondary antibody or streptavidin conjugated to HRP.

Statistical Analysis.

Statistical analysis was performed using Student's unpaired t test for DTH, mixed lymphocyte reactions, and cytokine assays. ANOVA was used to analyze allogeneic islet graft survival. P values of <0.05 were considered to be statistically significant.

Results

Streptozotocin-treated diabetic C57BL/6 recipients were injected i.v. with $10^8$ ECDI-treated BALB/c splenocytes 7 days before and 1 day after grafting of BALB/c islets under the kidney capsule (SEE FIG. 1A). Seventy percent of the recipients achieved indefinite (>100 days) graft survival (SEE FIG. 1B). To delineate the dose and timing requirement for effective tolerance induction, three parallel groups of mice received $10^8$ ECDI-treated BALB/c splenocytes at (i) one dose on day −7; (ii) one dose on day +1; or (iii) two doses on days −8 and −7. None of the three treatment protocols led to significant prolongation of graft survival (SEE FIGS. 1C and 1D). Protection is donor specific and ECDI dependent, because injections of $10^8$ ECDI-treated third-party strain SJL splenocytes on day −7 and day +1 did not protect transplanted BALB/c islets, and injection of untreated BALB/c splenocytes on day −7 and day +1 resulted in accelerated graft rejection (SEE FIG. 1B).

Figure 2:
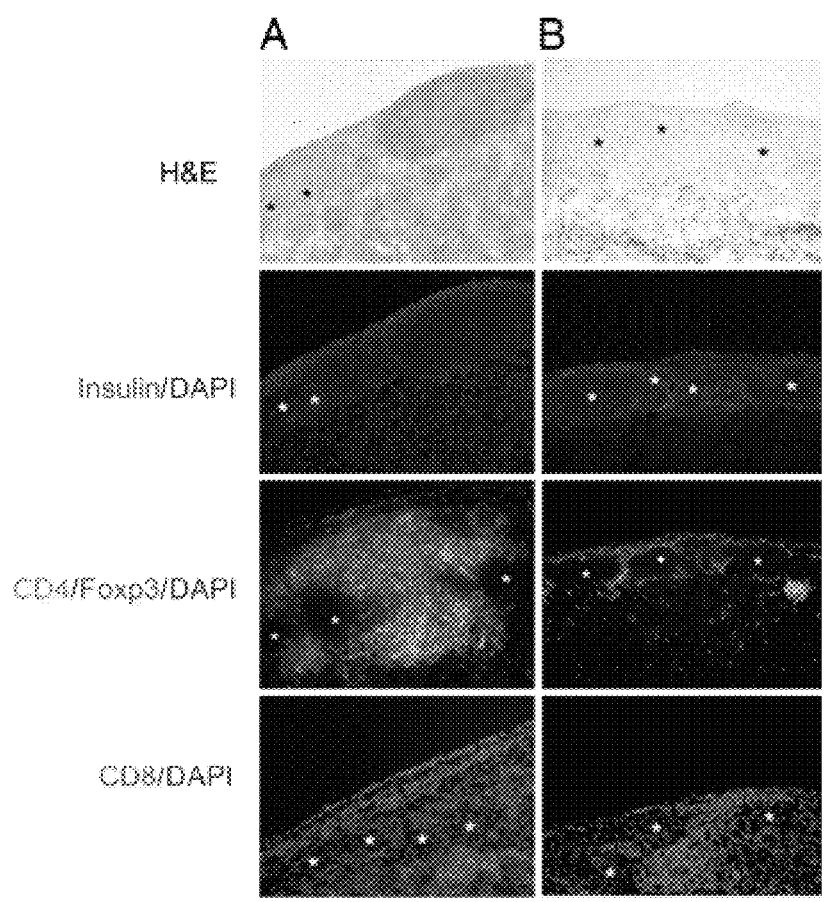
FIG. 2 shows graft histology results from Example 1. In particular.

Acutely rejecting grafts showed dense lymphocytic infiltrates with destruction of islet structures and complete absence of insulin production by the β cells. Over time, islets were replaced progressively by fibrous tissue. Protected grafts 14 days after transplantation (SEE FIG. 2A) showed intense peri-islet lymphocytic infiltrates that did not enter the islets or disrupt the islet structure. Furthermore, insulin production by these islets was readily detectable. Similar peri-islet infiltration was observed in long-term protected grafts (70 days after transplantation) (SEE FIG. 2B), but the number of infiltrating lymphocytes was considerably less than that observed in short-term protected grafts. Again, robust insulin secretion was maintained. Characterization of the infiltrating cells revealed the presence of CD4$^+$, CD8$^+$, and CD4$^+$Toxp3$^+$ T cells (SEE FIG. 2A-B).

Figure 3:
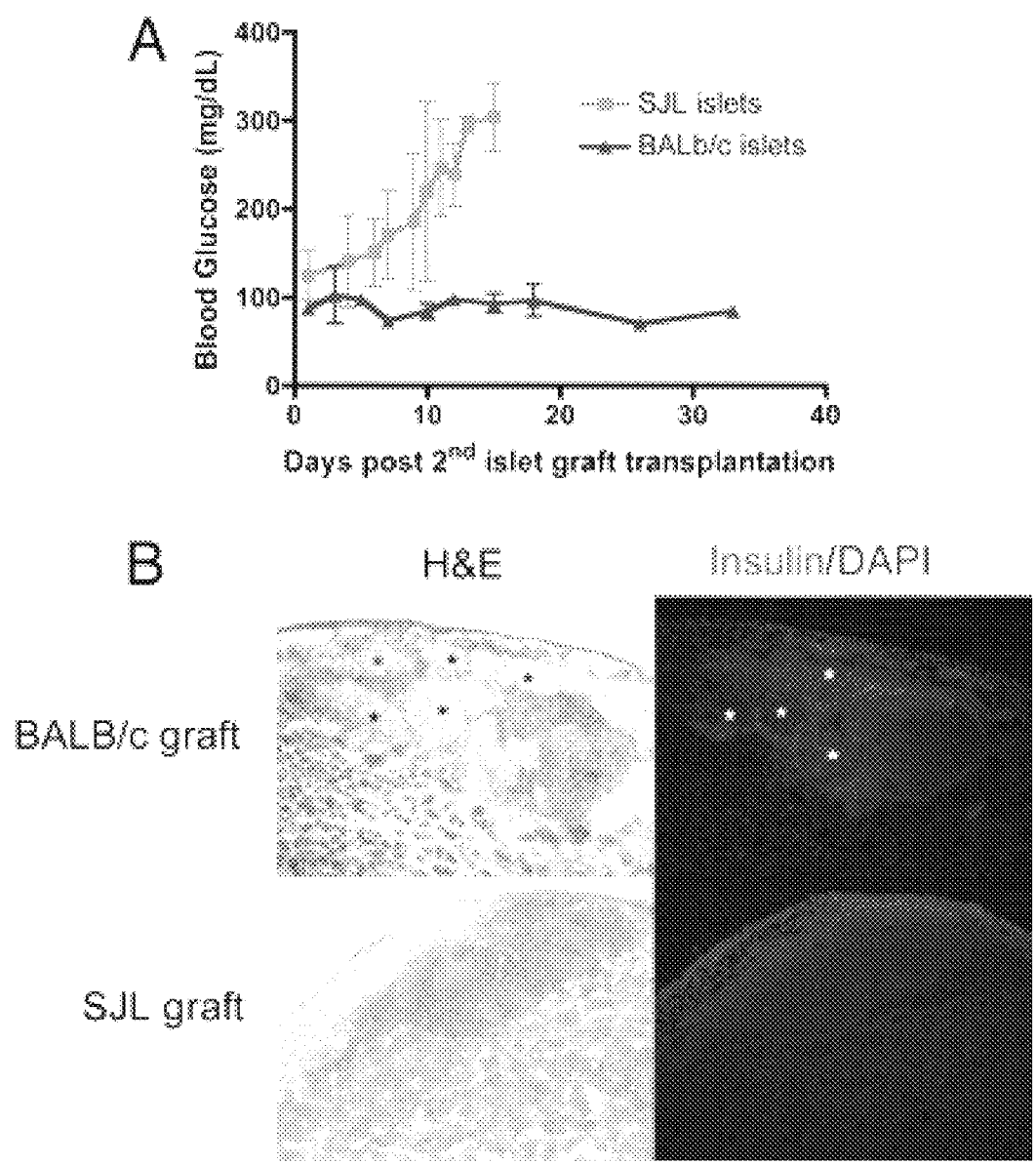
FIG. 3 shows results from Example 1 and particularly shows that long-term tolerized recipients show spontaneous acceptance of a second same-donor islet graft without further intervention.

Graft nephrectomy was performed to establish that long-term normoglycemia was caused by functioning grafts rather than incomplete streptozotocin. Within 48 hours after graft removal, the mice became hyperglycemic. Long-term tolerized recipients (60-90 days after initial transplantation) also were transplanted with a second same-donor (BALB/c) graft or with a third-party (SJL) graft without further treatment. These recipients accepted the BALB/c grafts without further manipulation but rejected the SJL grafts within the expected time frame (SEE FIG. 3A). Histology of the second BALB/c graft showed similar peri-islet infiltrates but intact islet architecture and robust insulin production (SEE FIG. 3B). Collectively, infusion with ECDI-treated donor cells resulted in durable donor-specific unresponsiveness.

Allogeneic Graft Protection is Associated with Antibodiesence of Anti-Donor Responses.

Delayed-type hypersensitivity (DTH) responses was examined around the time of expected acute allograft rejection (15 days after transplantation). Rejecting hosts showed robust DTH responses upon ear challenge with donor BALB/c cells (SEE FIG. 4A), but tolerized recipients showed a complete absence of DTH.

Donor-Specific Antibodies.

Next, the effect of tolerance on allo-specific β-cell activity was examined by measuring anti-donor antibodies of the IgG1, IgG2a, IgG2b, and IgG3 subclasses. Long-term (90 days after transplantation) tolerized recipients showed complete absence, whereas control rejected recipients showed robust antibody productions of all IgG subclasses (SEE FIG. 4B).

Mixed Lymphocyte Reactions and Cytokine Production.

Figure 4:
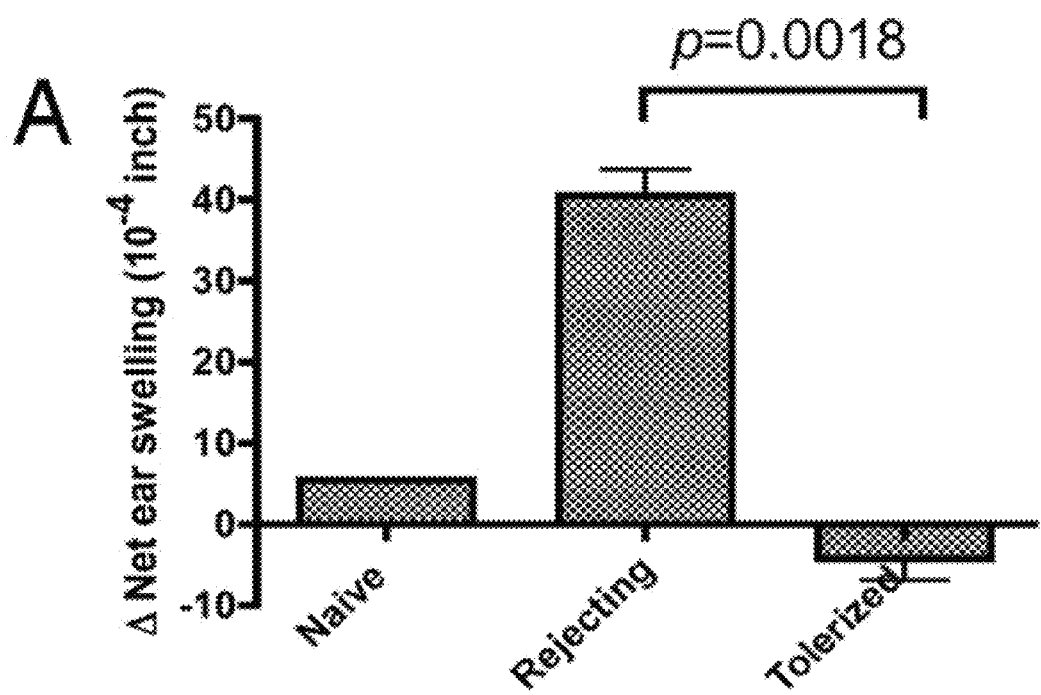
FIG. 4 shows results from Example 1 which demonstrated diminished alloantigen-specific T-cell and antibody responses are associated with protection of allogeneic islet grafts.
Figure 4:
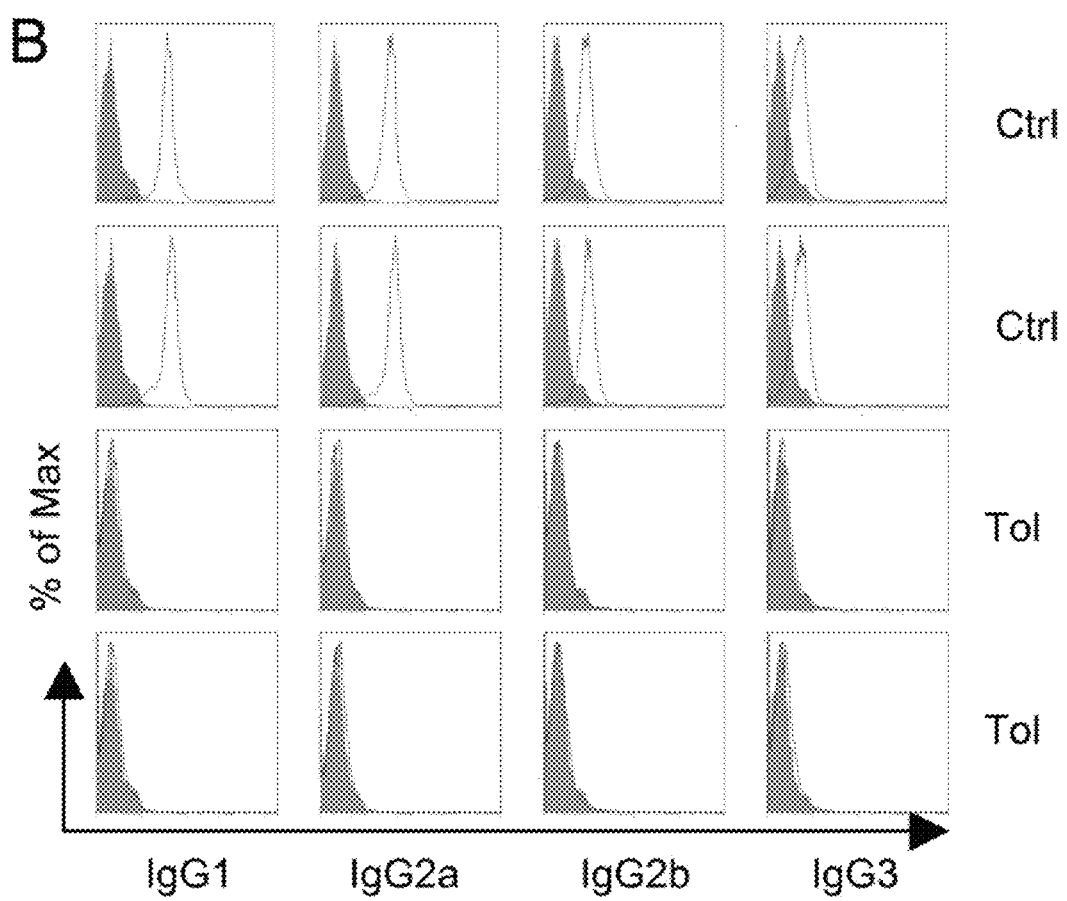
Figure 4:
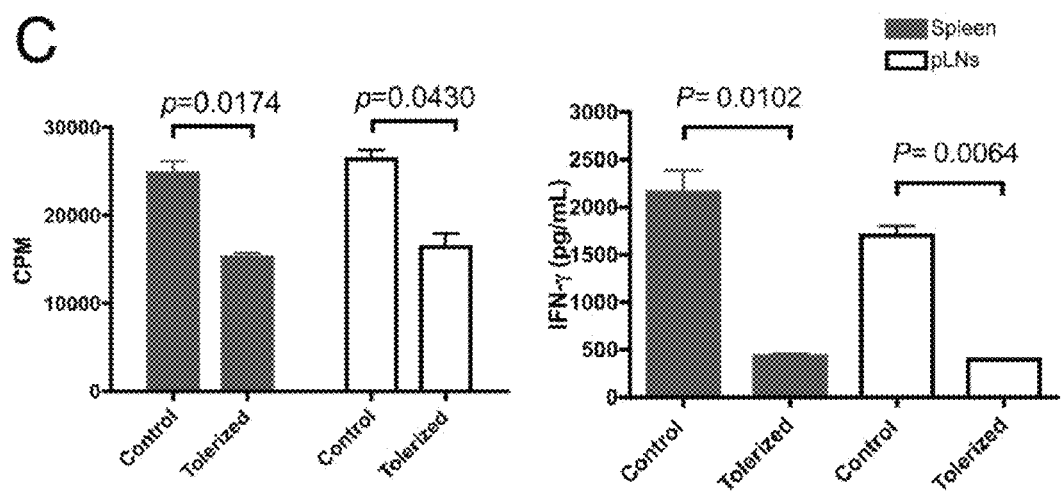

Compared with control recipients, T cells from the spleen or peripheral lymph nodes of tolerized recipients showed significantly diminished mixed lymphocyte reactions at the time of expected graft rejection (15-20 days after transplantation) as measured by $^3$H-thymidine uptake (SEE FIG. 4C. Furthermore, IFN-γ production was significantly inhibited (SEE FIG. 4C). No differences were observed in the production of IL-17, IL-10, or IL-4.

While the present invention is not limited to any particular mechanism, and an understanding of the mechanism is not necessary to practice the present invention, these data suggest that multiple effector functions of alloantigen-specific T and β cells are suppressed by this tolerance protocol.

Tolerance Induction, but Not Maintenance, is Dependent on $CD4^+CD25^+$ Regulatory T Cells.

Figure 5:
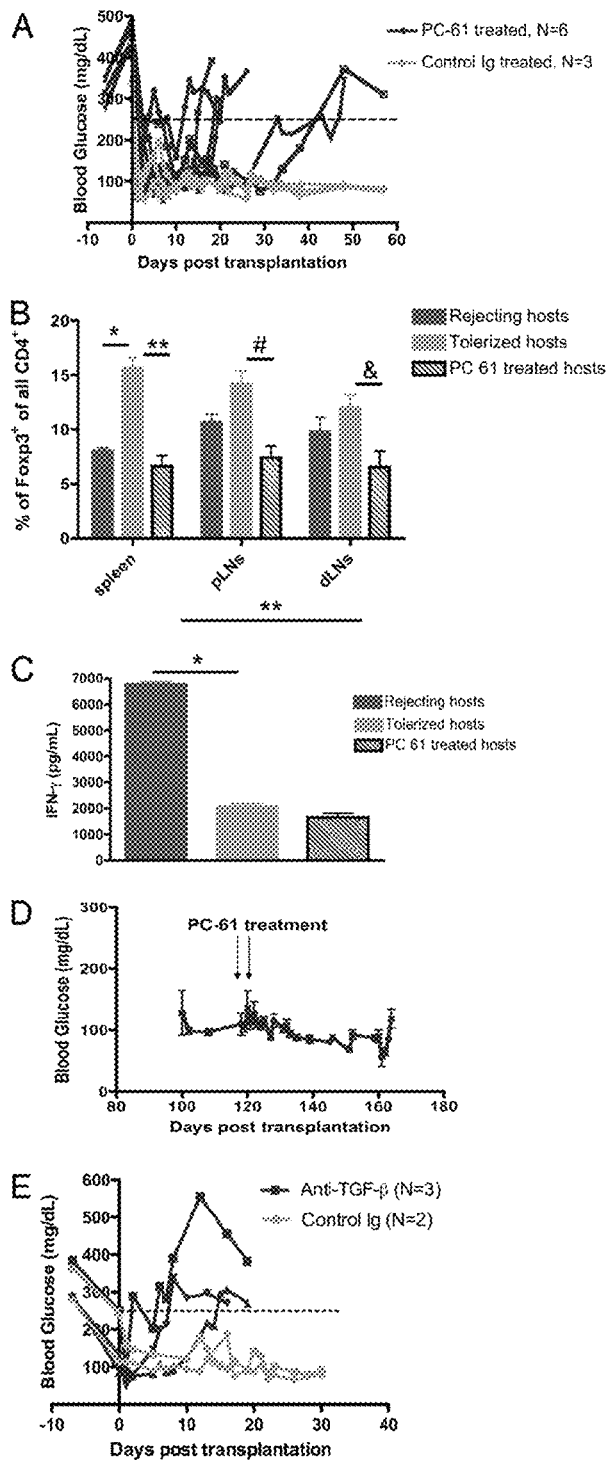
FIG. 5 shows that CD4$^+$CD25$^+$ Tregs are required for tolerance induction by i.v. treatment with ECDI-treated donor splenocytes but not for tolerance maintenance.

To examine the potential role of $CD4^+CD25^+$ Tregs in the induction and maintenance of tolerance using ECDI-treated donor-cell infusions, transplant recipients were treated with anti-CD25 mAb (PC61) to deplete/inactivate Tregs either before or after establishment of tolerance. Impairment of Tregs (by treatment with PC61 on days −9 and −7) around the time of initial tolerance induction (day −7) completely blocked tolerance induction, resulting in rejection of islet allografts in all six recipients, whereas the three Ig-treated tolerized control mice maintained glucose homeostasis for >60 days (SEE FIG. 5A). Thus, while the present invention is not limited to any particular mechanism, functional $CD25^+$ Tregs seem to be essential for tolerance initiation. This probability is supported further by data showing a greater number of $CD4^+CD25^+Foxp3^+$ Tregs in the spleen of tolerized mice as than in controls (SEE FIG. 5B). Correspondingly, PC61 treatment resulted in significant depletion in the number of $CD4^+CD25^+Foxp3^+$ cells in the spleen, peripheral lymph nodes, and lymph nodes draining the transplanted kidney (SEE FIG. 5B), concomitant with its ability to inhibit tolerance induction. Immunohistochemical analysis also showed the presence of significant numbers of $CD4^+Foxp3^+$ T cells in the peri-islet infiltrates in tolerized hosts, indicating that Tregs in the graft site may mediate local regulation of alloantigen-specific Teffs (SEE FIG. 2A). Donor antigen-specific IFN-γ response still was suppressed in PC61-treated mice, although these animals rejected the grafts (SEE FIG. 5C). This finding is consistent with previous observations that tolerance induced with peptide-coupled syngeneic APCs for treatment of EAE induces both direct anergy in autoreactive CD4 T cells and activation of Tregs (Miller S D, Turley D M, Podojil J R (2007) *Nat Rev Immunol* 7:665-677.; herein incorporated by reference in its entirety).

In contrast, PC61 treatment in long-term tolerized recipients (120 days after transplantation) did not break the established tolerance, because all treated mice remained normoglycemic during the ensuing observation period (SEE FIG. 5D) despite evidence showing an absence of $CD25^+$ cells in peri-islet infiltrates after PC61 treatment. While the present invention is not limited to any particular mechanism, it is believed that these results indicate that $CD4^+CD25^+$ Tregs are important for the initial establishment of the donor-specific tolerance, but active regulation is less important once tolerance has been established. Thus, other mechanisms, such as anergy, may be required for long-term maintenance of donor-specific unresponsiveness.

A study (Perruche S, et al. (2008) *NatMed* 14:528-535.; herein incorporated by reference in its entirety) of CD3- specific antibody-induced immune tolerance revealed an important role of TGF-β in the in vivo induction of $CD4^+Foxp3^+$ regulatory T cells. Experiments were conducted during development of embodiments of the present invention to determine whether TGF-β plays a role in tolerance by the protocol of this Example. Treatment with anti-TGF-β completely abolished tolerance induction, resulting in three of three grafts being rejected between posttransplantation day 6 and day 14 (SEE FIG. 5E). Therefore, it would appear that TGF-β plays an obligatory role in the tolerance induced by ECDI-treated donor cells.

Programmed Death-1/Programmed Death Ligand-1 Signaling is Crucial for Donor-Specific Tolerance Induced by Ethylene Carbodiimide-Treated Donor Splenocytes Experiments were conducted during development of embodiments of the present invention to determine whether cell-surface inhibitory molecules play a role in tolerance. The PD-1 pathway is up-regulated upon T-cell activation and has been implicated in controlling intrinsic T-cell function under tolerogenic conditions (Fife B T, et al. (2006) *J Exp Med* 203:2737-2747.; herein incorporated by reference in its entirety). Therefore, the efficacy of infusing ECDI-treated donor splenocytes was tested in diabetic PD-L1-deficient mice receiving BALB/c islet grafts. Untreated diabetic $PD-L1^{-/-}$ mice rejected BALB/c islet grafts with kinetics (SEE FIG. 6A) similar to those in untreated wild-type B6 recipients (SEE FIG. 1A). Long-term donor-specific tolerance was not induced in diabetic $PD-L1^{-/-}$ mice tolerized with ECDI-treated donor BALB/c splenocytes, because the majority of recipients rejected islet allografts within 10 to 20 days. These data suggest that the PD-1/PD-L1 signaling likely plays an important role in this tolerance regimen.

Figure 6:
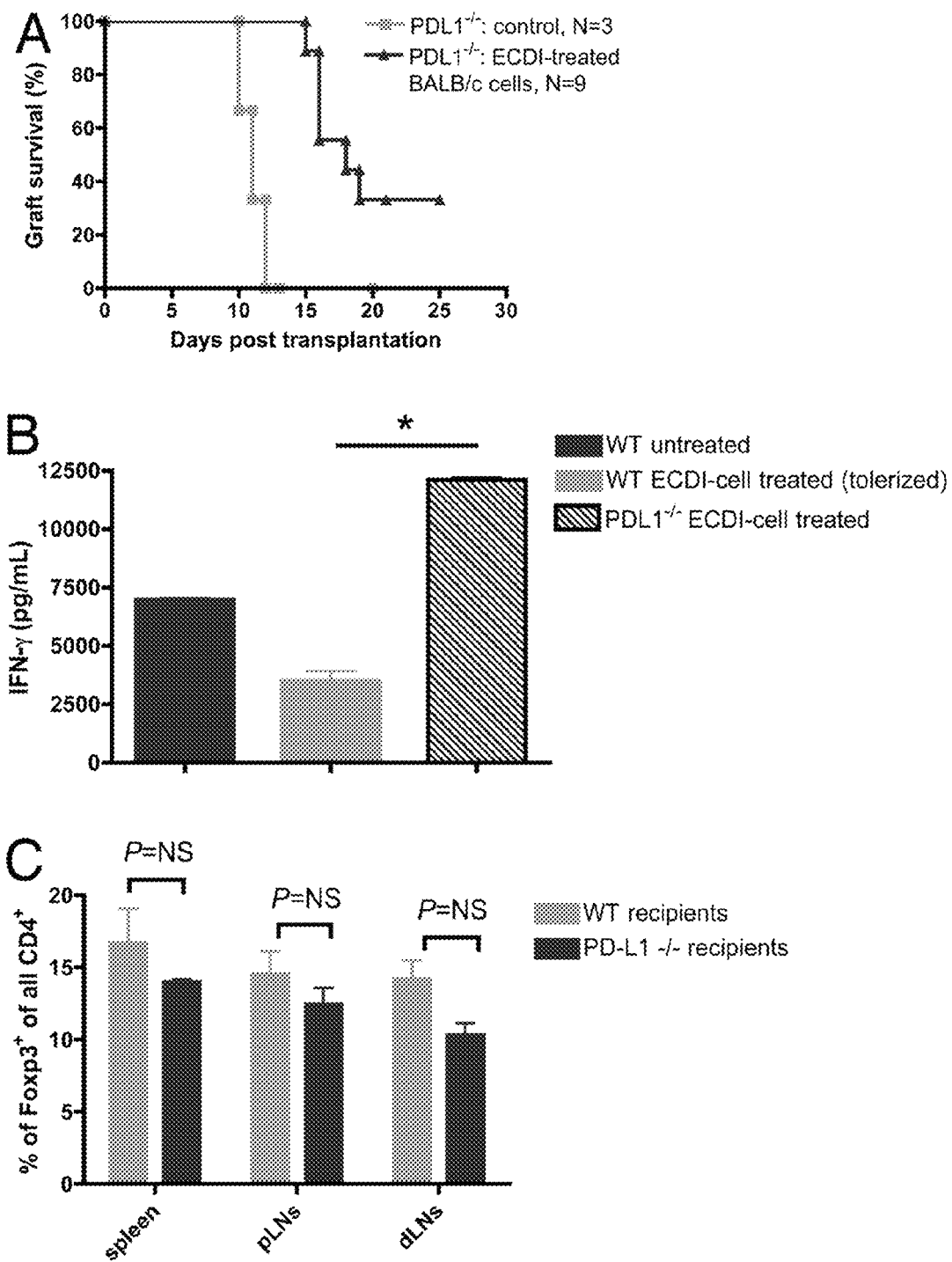
FIG. 6 shows the absence of PD-L1 signaling impairs tolerance induction mediated by the infusions of ECDI-treated donor cells.

Production of IFN-γ by splenic T cells from ECDI-treated $PD-L1^{-/-}$ recipients was enhanced significantly in comparison with T cells from wild-type tolerized recipients and even in comparison with T cells from wild-type untreated mice (SEE FIG. 6B). However, compared with untreated rejecting recipients (SEE FIG. 5B), the increase in the number of $CD4^+CD25^+Foxp3^+$ Tregs in the peripheral lymphoid organs of $PD-L1^{-/-}$ recipients of ECDI-treated cells and in wild-type tolerized hosts is similar (SEE FIG. 6C). While the present invention is not limited to any particular mechanism, these data suggest that, whereas PD-1/PD-L1-negative signaling plays an important role in the initial induction of tolerance by down-regulating donor-specific IFN-γ responses, the expansion and/or induction of the Treg population by ECDI treatment is independent of the PD-1/PD-L1 pathway.

In this example, it is shown that two infusions of ECDI-treated donor splenocytes (one before and one after infusion) lead to long-term or permanent acceptance of allogeneic islet grafts in fully immunocompetent recipients without the need for immunosuppression. The tolerance state induced by the ECDI-treated donor cells is donor-specific and is associated with markedly diminished donor-specific allo-responses. Tolerance by this protocol would appear to be mediated through a PD-1/PD-L1-dependent down-regulation of Teff activity and an independent up-regulation of Tregs. However, once tolerance is established, Treg impairment does not break the tolerant state, and the hosts accept a second same-donor graft long-term or indefinitely without further intervention.

One important difference between the tolerance protocol in this Example and others using infusions of donor cells (e.g., donor-specific transfusion) is that efficient induction of tolerance is achieved in the complete absence of immunosuppression, including transient cell depletion, antibody-mediated blockade of costimulatory signals, or peri-transplantation application of immunosuppressive drugs.

Cell ablation around the time of transplantation is thought to debulk alloreactive T cells, which are present at high frequencies (Bushell A, Morris P J, Wood K J (1995) *Eur J Immunol* 25:2643-2649.; Xia G, He J, Leventhal J R (2008) *Am J Transplant* 8:298-306.; herein incorporated by reference in their entireties), inducing a favorable ratio of regulatory cells to effector cells. Increasing understanding of Treg biology has resulted in cell therapy using allogeneic transplantation of ex vivo expanded $CD4^+CD25^+$ Tregs in animal models, and this strategy now is being tested clinically (Bluestone J A (2005) Regulatory T-cell therapy: Is it ready for the clinic? *Nat Rev Immunol* 5:343-349.; herein incorporated by reference in its entirety). However, several rounds of ex vivo stimulation are required to obtain sufficient numbers of Tregs for in vivo suppression (Koenen H J, Joosten I (2006) *Hum Immunol* 67:665-675.; herein incorporated by reference in its entirety), and initial depletion of recipient T cells still is required for its success. Several other approaches are now in human trials in solid-organ transplantation, including infusion of donor bone marrow stem cells with or without induction of mixed chimerism (Kawai T, et al. (2008) *N Engl J Med* 358:353-361.; Scandling J D, et al. (2008) *N Engl J Med* 358:362-368.; herein incorporated by reference in their entireties). Similarly, these approaches also require initial myeloablation, which is associated with significant comorbidities. The fact that infusion of ECDI-treated donor cells induces durable tolerance in the absence of any immunosuppression makes the methods of the present invention highly desirable.

In islet cell transplantation, another concern is recurrent autoimmunity toward the transplanted β cells. Similar to published work in EAE (Turley D M, Miller S D (2007) *J Immunol* 178:2212-2220.; herein incorporated by reference in its entirety), the data in this Example indicates that tolerance induced with ECDI-fixed syngeneic APCs coupled with either the immunodominant insulin peptide $InsB_{9-23}$ or intact insulin prevents onset of diabetes or induces remission in new-onset disease, respectively, in NOD mice. This finding confirms earlier data showing that $InsB_{9-23}$ probably is the initiating diabetogenic epitope in NOD (Nakayama, M, et al. (2005) *Nature* 435:220-223.; herein incorporated by reference in its entirety). Therefore, ECDI-treated cells potentially can induce tolerance in both alloantigens and the insulin autoantigen, thereby preventing rejection of the allogeneic islet graft and recurrence of autoimmunity in patients who have type-1 diabetes.

The exact mechanism with which ECDI-treated cells induce donor-specific tolerance is not completely understood and is not necessary to understand to practice the present invention. Recent studies indicate that ECDI treatment induces the cells to undergo rapid apoptosis and that tolerance is induced by both direct and indirect antigen presentation (Turley D M, Miller S D (2007) *J Immunol* 178:2212-2220.; herein incorporated by reference in its entirety). Cell tracking indicates that ECDI-treated cells distribute widely, but intact cells disappear within 48 hours. Therefore, although direct presentation may play a role, this mechanism probably is transient. In contrast, indirect presentation of alloantigens by host regulatory APCs probably is the predominant tolerance mechanism. Other models of allogeneic transplantation also indicate that the indirect pathway plays a critical role in donor-specific tolerance (Ochando J C, et al. (2006) *Nat Immunol* 7:652-662.; Joffre O, et al. (2008) *Nat Med* 14:88-92.; herein incorporated by reference in their entireties). Recent data in the EAE model suggest that host plasmacytoid dendritic cells are crucial in this tolerogenic cross-presentation and that the tolerogenic interactions probably occur in the spleen.

While the present invention is not limited to any particular mechanism, the depletion of Tregs around the time the first injection of the ECDI-treated donor cells abolished tolerance induction suggests that initial presence of Tregs is important for conferring the tolerant state. However, as seen in the control animals, once the process of rejection begins, the number of Tregs observed both in the peripheral lymphoid organs and in the rejecting grafts increases as compared with naïve hosts. This phenomenon has been observed previously in other models of graft rejection (Muthukumar T, et al. (2005) *N Engl J Med* 353:2342-2351.; Schneider T M, et al. (1986) *Transplantation* 42:191-196.; herein incorporated by reference in their entireties) and may represent an intrinsic attempt by the host to control inflammation that ultimately fails, probably because of an unfavorable Treg:Teff balance. While the present invention is not limited to any particular mechanism, infusion of ECDI-treated donor cells probably promotes early establishment of a favorable Treg:Teff ratio and possibly enhances Treg function. It therefore is intriguing that, once tolerance is established in the methods of this Example, depletion of Tregs does not ameliorate the tolerant state. It is possible that donor-specific Teff cells are kept effectively in a state of anergy by continuous interaction with the tolerated graft. The anergy hypothesis is supported by persistently depressed proliferation and IFN-γ production by T cells in mixed lymphocyte reaction cultures (data not shown) and by the significantly fewer numbers of $Foxp3^+$ T cells in the graft bed observed in the long-term tolerized hosts (SEE FIGS. 2A/B) and by similarly depressed T-cell responses in hosts tolerized after Treg depletion (SEE FIG. 5C). Therefore, anergy may be the major mechanism for tolerance maintenance, as suggested in other models of tolerance (Cook C H, et al. (2008) *J Immunol* 180:3103-3112.; herein incorporated by reference in its entirety).

The importance of PD-1/PD-L1-negative signaling unresponsiveness induced in ECDI-treated cells was substantiated further by the observation that tolerance induction was disrupted significantly in $PD-L1^{-/-}$ recipients. PD-L1 is widely expressed on leukocytes and in nonlymphoid tissues including the pancreatic islets (Greenwald R J, Freeman G J, Sharpe A H (2005) *Annu Rev Immunol* 23:515-548.; herein incorporated by reference in its entirety), although PD-1/PD-L1 signaling in the graft site is clearly not sufficient for induction of tolerance because PD-L1-sufficient mice were used as islet donors. It is interesting that ECDI-treated donor cell infusions induced a similar increase in Tregs in both wild-type and $PD-L1^{-/-}$ recipients, suggesting that the induction and/or expansion of Tregs by the protocol in this Example is independent of PD-L1 signaling. In addition, suppression of IFN-γ production was abolished in $PD-L1^{-/-}$ recipients, suggesting a direct effect of PD-1 signaling on Teff cells. Because ECDI-fixed cell tolerance also was prevented by depletion of Tregs, the data in this Example collectively suggest that both T-cell anergy and T-cell regulation are involved independently in the process of tolerance induction. During the initial phase of tolerance, it is important to establish a favorable Treg:Teff cell balance, both in numbers and in function. Consequently, impairment of such a balance, either by impairing Tregs with anti-CD25 antibody or by blocking Teff cell anergy via the PD-1/PD-L1 pathway, results in failure of tolerance induction.

Example 2

ECDI-Treated Splenocytes Carrying Male CD4 Epitopes Confer Histocompatability Y Chromosome Antigen Transplant Protection Materials and Methods Mice Age-matched male and female C57BL/6 (B6) mice and homozygous OT-II mice used for experiments conducted during development of embodiments of the present invention were housed in the Center for Comparative Medicine in sterile microisolator cages with ad libitum access to water and chow.

Tolerance Induction

Splenocytes (SPs) were coupled to antigens in the presence of 30 mg/ml ECDI and 1 mg/ml peptide (Miller et al. 1979. *J. Exp. Med.* 149: 758-773; herein incorporated by reference in its entirety). For tolerance induction to male antigens in B6 females, $10^8$ antigen-SPs were administered i.v. for 7 d and again 3 h prior to engraftment. B6 females received antigen-SP coupled to either the CD4 epitope found in male antigen (Dby:NAGFNSNRANSSRSS) or two CD8 epitopes (Uty: WMHHNMDLI, Smcy:KCSRNRQYL) added at equimolar ratios. Tolerance in OT-II mice was induced by i.v. injection of $10^8$ $OVA_{323-339}$-SPs (ISQAVHAAHAEINEAGR) 7d prior to assay.

Skin Grafting

Orthotopic split-thickness tail skin grafting was performed (Busker, A. E., S. D. Miller, R. W. Melvold. 1990. Induction of allograft tolerance to the H-Y antigen in adult C57BL/6 mice: differential effects on delayed-type hypersensitivity and cytolytic T-lymphocyte activity. *Cell. Immunol.* 125: 225-234.; herein incorporated by reference in its entirety). Grafts were scored by daily visual inspection for edema, pigment loss, and hair loss. Rejection was defined by complete hair loss and >80% pigment loss. Differences in survival times were tested for significance by log-rank tests.

T Cell Recall Assays

Animals were sacrificed at the indicated times posttransplantation. Single-cell suspensions of spleen and draining lymph nodes were explanted into 96-well plates and challenged with Dby, Uty, Smcy, or $OVA_{323-339}$ (irrelevant antigen control) peptides (0.05-5 μM). Anti-CD3 (2C11) stimulation was included as a control for proliferation and cytokine secretion. Cultures were grown in RPMI 1640 supplemented with 10% heat-inactivated FBS, 1% penicillin/streptomycin, 50 μM 2-ME, and 25 mM HEPES buffer for 72 h. Proliferation was measured by pulsing with 1 μCi[$^3$H]thymidine at 48 h and harvesting 24 h later. Culture supernatants were collected at 72 h, and cytokine secretion was measured by ELISA using anti-IFN-γ clones XMG1.2 (capture) and biotin-R4-6A2 (detection) (eBioscience, San Diego, Calif.), streptavidin-HRP, and enzyme substrate (BioFX, Owing Mills, Md.). $OVA_{323-339}$ responses in naive or treated OT-II mice were measured similarly.

In Vivo CTL Assays

Target cells were labeled with 5 and 0.5 μM concentrations of carboxyfluorescein diacetate (Invitrogen/Molecular Probes, Carlsbad, Calif.) at room temperature for 8 min and quenched in the presence of 20% heat-inactivated FBS for 5 min, allowing distinct identification by flow cytometry (Getts, M. T., B. S. Kim, S. D. Miller. 2007. *J. Virol.* 81: 6584-6593.; herein incorporated by reference in their entireties). Fluorescently labeled cells were counted and mixed at a 1:1 ratio prior to i.v. injection. Targets were loaded with antigens (5 μM) for 90 min at 37° C., and cytometric analyses of recipient spleens were performed 6 d following i.v. transfer.

Antibodies and Flow Cytometry

Allophycocyanin-conjugated H-2D$^b$ tetramers specific for Uty and Smcy TCRs were used in experiments conducted during embodiments of the present invention. Other primary conjugates used in this study include CD44-PE/Cy7, CD62L-allophycocyanin/Alexa Fluor 750, CD69-FITC, CD127-biotin, CD40-FITC, CD154-PE (CD40L), CD8-eFluor605, CD4-allophycocyanin, and CD3-Pacific blue or PerCP (eBioscience). Live-dead discrimination was performed using LIVE/DEAD fixable staining reagents (Invitrogen). Detection of biotinylated reagents was accomplished using streptavidin-PE/Cy7 (eBioscience). For analyses of cultured cells, dead cells were excluded from analysis using Violet Dead Cell Stain (Invitrogen/Molecular Probes). Flow cytometric analyses were carried out using a FACSCanto II (BD Biosciences, Franklin Lakes, N.J.). Data were collected and analyzed using FACSDiVa software. Anti-CD40 (FGK45.5) and isotype control rIgG2a were purchased from Miltenyi Biotec (Auburn, Calif.).

Skin Graft Histology

Mouse tails were fixed in 4% paraformaldehyde in PBS overnight at 4° C. followed by infiltration with 30% sucrose in PBS overnight at 4° C. Sections containing grafts were frozen in cryomolds in OCT on dry ice and sectioned at 10 μm with a cryostat. Prior to being labeled, sections were air-dried at room temperature for at least 30 min, rinsed in distilled water to remove OCT, and fixed in −20° C. acetone for 10 min. Sections were dried at room temperature for 10 min, washed in PBS three times for 5 min, and blocked in 5% normal donkey serum in PBS and 0.1% Triton X-100 (PBS+) for 60 min prior to incubation with primary antibodies in PBS+ overnight at 4° C. After being washed in PBS three times for 10 min, sections were incubated in secondary antibodies in PBS+ for 1 h at room temperature, washed in PBS three times for 10 min, incubated in DAPI for nuclear staining for 5 min, washed three times for 5 min in PBS, and then covered with a coverslip using hard setting VECTAMOUNT (Vector Laboratories, Burlingame, Calif.). For biotinylated primaries, peroxidase block (DakoCytomation, Carpinteria, Calif.) was used for 30 min followed by streptavidin/biotin block (Vector Laboratories) prior to the PBS+ blocking step. The streptavidin/tyramide system (PerkinElmer Life Sciences, Downers Grove, Ill.) was used to visualize biotinylated primary antibodies. Antibodies used include: anti-mouse CD4 (eBioscience), anti-mouse CD8, (Santa Cruz Biotechnology, Santa Cruz, Calif.), and anti-mouse F4/80 (Invitrogen). Images were taken on a DM 5000B microscope (Leica Microsystems, Bannockburn, Ill.) using ImagePro software (Media-Cybernetics, Bethesda, Md.).

Results

Figure 7:
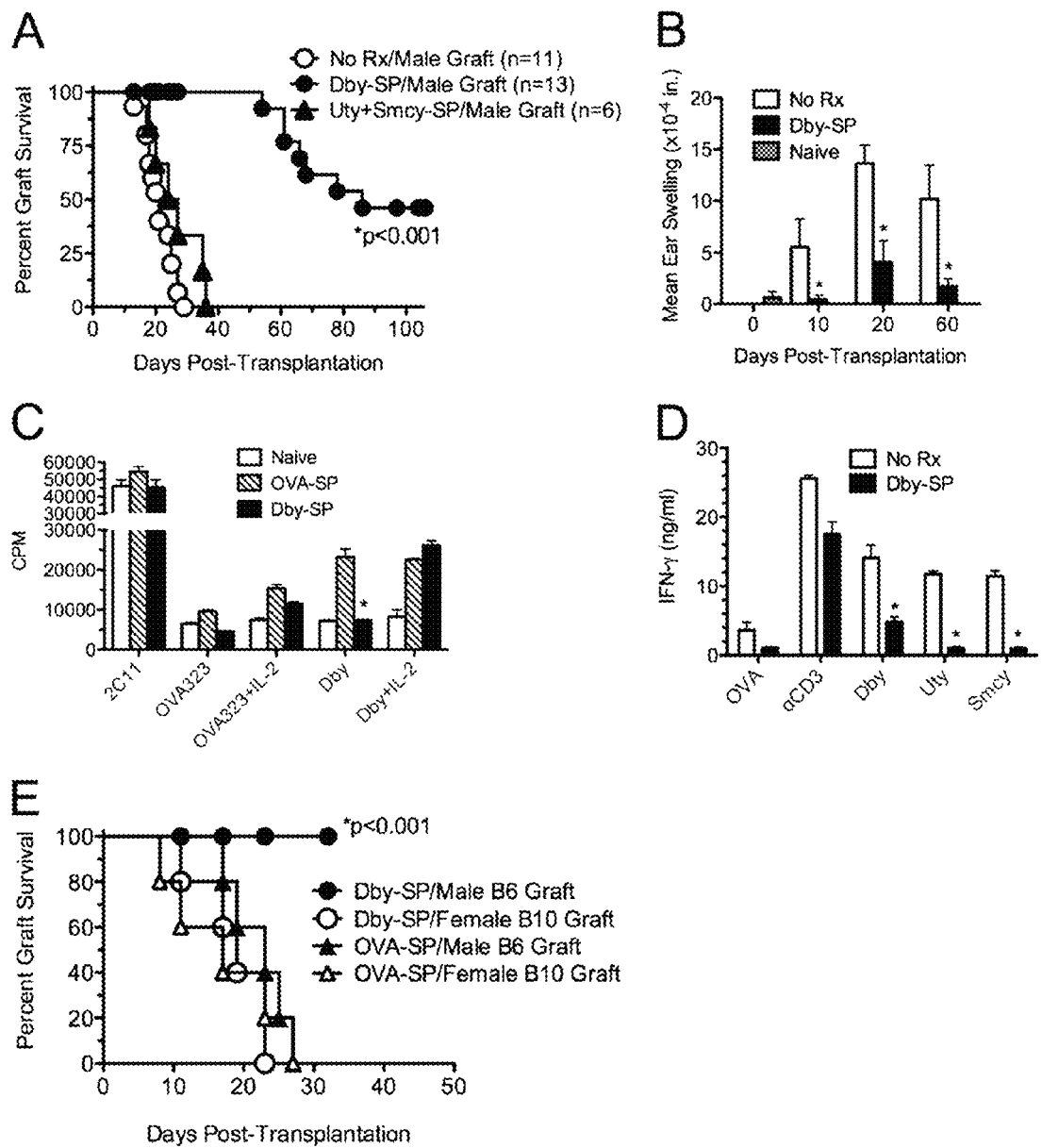
FIG. 7 shows Hya-specific MHC class II, but not MHC class I, restricted Hya epitopes ECDI-coupled to B6 female-derived splenocytes promote long-term, antigen-specific survival of male skin grafts on B6 female recipients.

Treatment with Splenocytes ECDI-Coupled with the Hya-Specific MHC Class II-Restricted Dby Epitope Promotes Long-Term Survival of B6 Male Skin Grafts Females of mouse strains with the H2$^b$ haplotype (e.g., B6) generate strong cellular immune responses against Hya-disparate tissue, as measured by allograft rejection kinetics and by the development of Hya-specific delayed-type hypersensitivity (DTH) and CTL responses (Simpson, E., D. Scott, P. Chandler. 1997. *Annu. Rev. Immunol.* 15: 39-61; herein incorporated by reference in its entirety). Naive B6 females were treated i.v. with either ECDI-fixed B6 male splenocytes or Dby-SPs (syngeneic female SPs ECDI-coupled with the Hya CD4 epitope) or with Uty/Smcy-SPs (female splenocytes ECDI-coupled with the Hya CD8 epitopes Uty and Smcy) on days −7 and 0 relative to engraftment with male tail skin. Male grafts survived for significantly longer times on Dby-SP-treated animals (median 77 d) than those on untreated animals (median 21 d) or Uty/Smcy-SP-treated animals (median 27 d) (SEE FIG. 7A). Antigen specificity of antigen-SP therapy was tested by engrafting treated and nontreated females with skin from third-party female C57BL/10 donors. Both nonprotected and Dby-SP-treated females rejected B10 grafts with equivalent kinetics (SEE FIG. 7E, median 17 d), indicating that Dby-SP specifically regulates Hya-expressing grafts. Furthermore, protection of male B6 grafts is not observed in animals treated with splenocytes coupled to an irrelevant antigen. $OVA_{323-339}$-SP-treated recipients rejected male grafts at a median of 22 d. Female B6 control grafts were not rejected by any treatment group and survived indefinitely.

Dby-SP treatment suppressed Dby-specific CD4 recall responses as determined by both in vivo DTH (examined longitudinally, SEE FIG. 7B) and in vitro proliferation (SEE FIG. 7C) and IFN-γ (SEE FIG. 7D), assessed 14 d posttransplant. These observations demonstrate that antigen-SP tolerance results in antigen-specific decreases in effector CD4 Th1/17 cell responses (Miller, S. D., D. M. Turley, J. R. Podojil. 2007. *Nat. Rev. Immunol.* 7: 665-67.; Miller, S. D., R. P. Wetzig, H. N. Claman. 1979. *J. Exp. Med.* 149: 758-773.; herein incorporated by reference in their entireties). Addition of 25 U/ml exogenous IL-2 to recall cultures restored [$^3$H] thymidine uptake by T cells from Dby-SP-treated recipients (SEE FIG. 7C), indicating that anergy plays a significant role in the Dby-SP-induced unresponsiveness (Jenkins, M. K., R. H. Schwartz. 1987. *J. Exp. Med.* 165: 302-319.; herein incorporated by reference in its entirety).

IFN-γ responses to the Hya CD8 epitopes, Uty and Smcy, were suppressed in Dby-SP-tolerant animals (SEE FIG. 7D). These findings indicate that antigen-SP treatment targeting the immunodominant Hya CD4 epitope (Dby) is necessary and sufficient to prolong the survival of male tissue grafts and that tolerance to the CD4 epitope results in priming failure of Hya-specific CD8 T cell responses. CD8$^+$ populations in Uty/Smcy-SP-treated animals also exhibit diminished functional responses.

Hya-Specific CD8 Cells Display a Naive Phenotype in Dby-SP-Tolerant Animals

Figure 8:
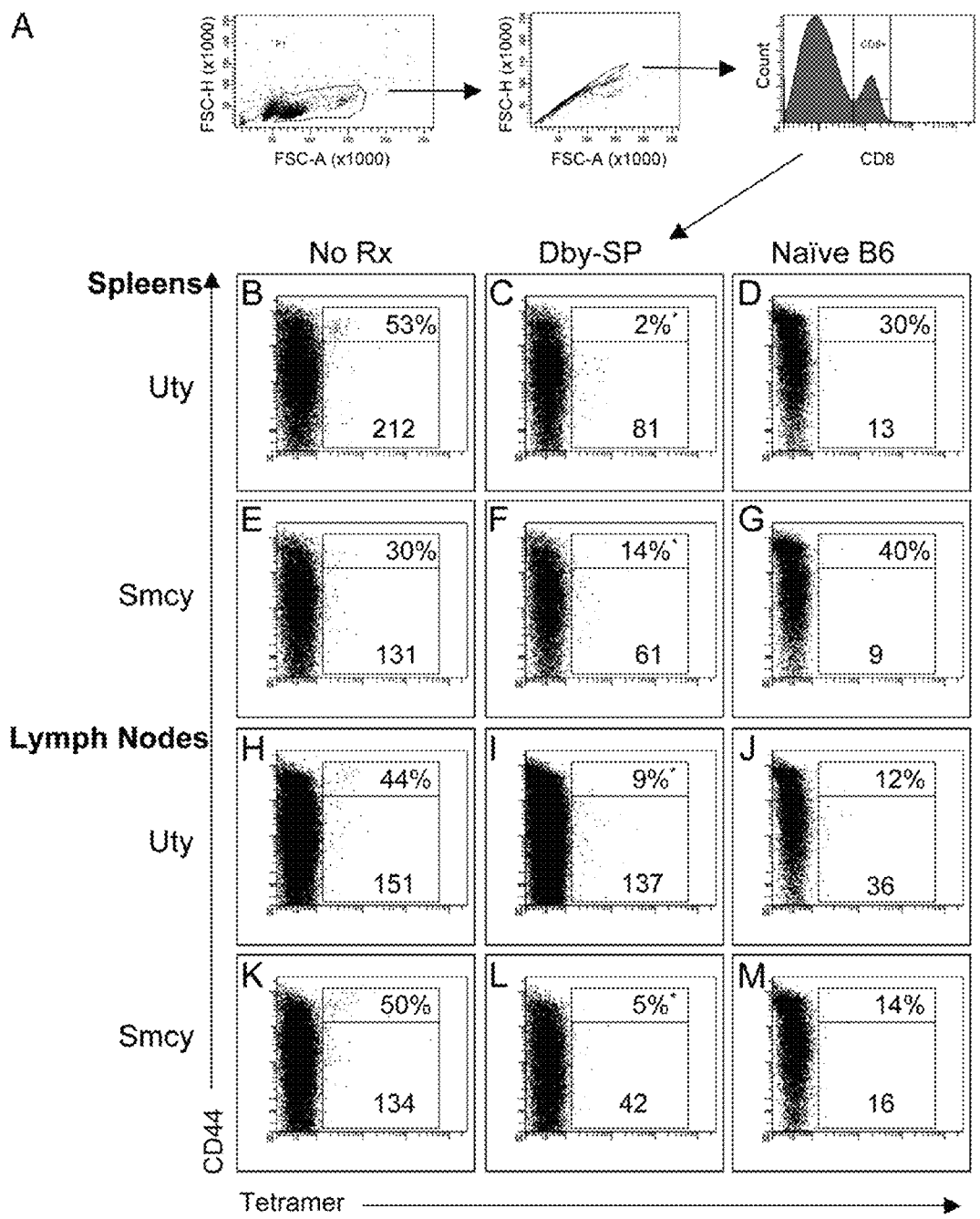
FIG. 8 shows that Dby-SP-induced nonresponsivenss of Hya-specific CD4+ T cells leads to failed priming of Hya-specific CD8+ T cells specific for the Smcy and Uty epitopes. The activation frequency (CD44+) of Hya Uty and Smcy epitope-specific CD8+ T cells was determined using MHC class I tetramers.
Figure 9:
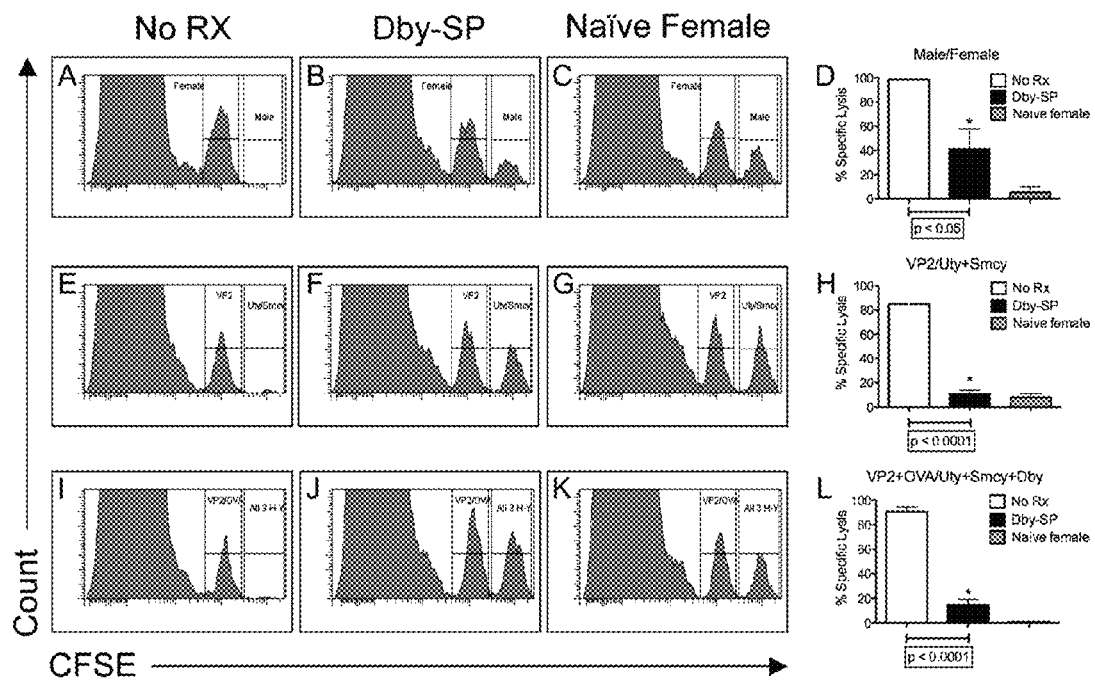
FIG. 9 shows Dby-SP-induced nonresponsivenss of Hya-specific CD4$^+$ T cells results in diminished cytolytic activity of Hya-specific CD8$^+$ T cells specific for the Smcy and Uty epitopes. B6 females were ungrafted (naive), untreated (No Rx), or i.v. tolerized with Dby-SPs prior to engraftment with male skin. Fourteen days later, in vivo Hya-specific cytolytic activity was determined. Peptide-loaded targets were administered (one specific target and one reference target) and were discernable by differential CFSE labeling.

To further investigate the effects of CD4 tolerance on the development of CD8 effector responses, the activation and lytic capacity of CD8 T cells specific for Uty and Smcy in the spleens and draining lymph nodes of control and Dby-SP-tolerized male graft recipients was measured. H-2D$^b$ tetramers identifying the Uty- and Smcy-specific TCRs were used to identify expression of the activation marker CD44 on Hya-specific CD8$^+$ populations. Compared to naive, nonengrafted B6 females, nontolerant graft recipients contain a distinct population of activated (CD44$^+$) Hya-specific CD8$^+$ T cells (SEE FIG. 8). Dby-SP treatment significantly inhibited the expansion and activation of Hya-specific CTLs, as demonstrated by a diminished number and proportion of tetramer-positive CD44$^+$ cells in both spleens and graft draining lymph nodes of tolerant animals. FIG. 8 displays data collected at day 14 posttransplantation. Similar results were observed 10, 20, or 40 d posttransplantation, although day 14 was the peak in Uty- and Smcy-specific CD8 cells in rejecting controls. This finding also coincides with an observed diminution of in vitro proliferative responses against Uty and Smcy following Dby-SP treatment. To assess the functional lytic capacity of Hya-specific CD8$^+$ T cells, we conducted in vivo cytolysis assays using a variety of target pairs differentially labeled with CFSE. Specific targets consisted of male splenocytes, female splenocytes pulsed with CD8 Hya epitopes (Uty and Smcy), or female splenocytes pulsed with all three Hya epitopes. These targets were paired with reference targets consisting of female splenocytes, female splenocytes pulsed with an irrelevant CD8 epitope (Theiler's murine encephalomyelitis virus [TMEV] viral protein 2 [VP2]), or female splenocytes pulsed with an irrelevant CD8 epitope (VP2) and an irrelevant CD4 epitope ($OVA_{323-339}$), respectively. Consistent with the phenotypic analyses, CD8$^+$ cells in Dby-tolerant animals failed to lyse male splenocytes or female splenocytes presenting male antigen (SEE FIG. 9). The results from both the tetramer analyses and lysis assays indicate that CD4$^+$ Th cells in Dby-SP-tolerant animals fail to prime effective Hya-specific CTL responses.

Antigen-SP Treatment Decreases CD154 Upregulation by Th Cells

Figure 10:
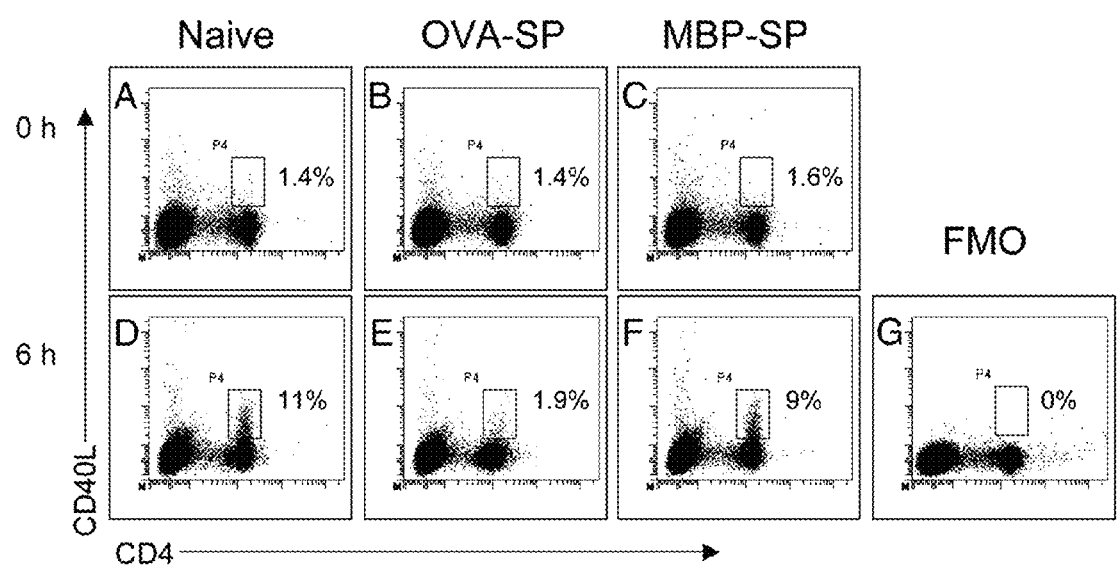
FIG. 10 shows antigen-SP treatment inhibits CD154 upregulation on antigen-specific CD4$^+$ T cells upon antigen recall.

Due to the failed priming of the antigen-specific CD8 compartment observed in animals tolerized against the immunodominant Hya-specific Dby CD4 epitope, we reasoned that there is possibly a defect in one or more of the mechanisms used by CD4$^+$ Th cells to prime Hya-specific CTLs. Defective IL-2 secretion by Th cells has been observed secondary to antigen-SP treatment (Peterson, J. D., W. J. Karpus, R. J. Clatch, S. D. Miller. 1993. *Eur. J. Immunol.* 23: 46-55.; Smith, C. E., T. N. Eagar, J. L. Strominger, S. D. Miller. 2005. *Proc. Natl. Acad. Sci. USA* 102: 9595-9600.; herein incorporated by reference in their entireties). A defect in IFN-γ synthesis has also been demonstrated to occur secondary to antigen-SP treatment (SEE FIG. 8). Upstream of both of these cytokines is the involvement of CD40/CD154, a TNF family receptor-ligand pair that is critical for T cell costimulation, licensing of APCs, and Th-dependent activation of CD8$^+$ T cells (Elgueta, R., M. J. Benson, V. C. de Vries, A. Wasiuk, Y. Guo, R. J. Noelle. 2009. *Immunol. Rev.* 229: 152-172.; herein incorporated by reference in its entirety). CD40 ligation on APCs by CD154 expressed by activated CD4$^+$ T cells increases APC expression of B7 family costimulatory molecules and proinflammatory cytokines, enabling the differentiation of naive CD8$^+$ T cells to functional cytolytic effectors (Williams, M. A., M. J. Bevan. 2007. *Annu. Rev. Immunol.* 25: 171-192.; Castellino, F., R. N. Germain. 2006. *Annu. Rev. Immunol.* 24: 519-540.; Elgueta, R., M. J. Benson, V. C. de Vries, A. Wasiuk, Y. Guo, R. J. Noelle. 2009. *Immunol. Rev.* 229: 152-172.; herein incorporated by reference in their entireties). Experiments were conducted during development of embodiments of the present invention to measure the ability of CD4$^+$ T cells to upregulate surface CD154 (CD40L) following treatment with antigen-SPs. OT-II TCR transgenic mice were left untreated (naive) or tolerized via the i.v. injection of 10$^8$ $OVA_{323-339}$-SPs or myelin basic protein $(MBP)_{84-104}$-SPs. Seven days later, spleens were removed and live CD4$^+$ cells were analyzed for CD154 surface expression immediately upon explant and at serial time points (6, 12, 24, 48, and 72 h) poststimulation with $OVA_{323-339}$ in vitro. Peak expression was observed 6 h poststimulation. Upon antigen encounter, a significantly lower frequency of CD4$^+$CD154$^+$ T cells was detected in cultures from mice tolerized to $OVA_{323-339}$-SPs in comparison with naive mice or mice tolerized to $MBP_{84-104}$-SPs, suggesting that antigen-SP encounter results in suboptimal activation and a decreased ability to present CD154 to other leukocytes (SEE FIG. 10).

Figure 11:
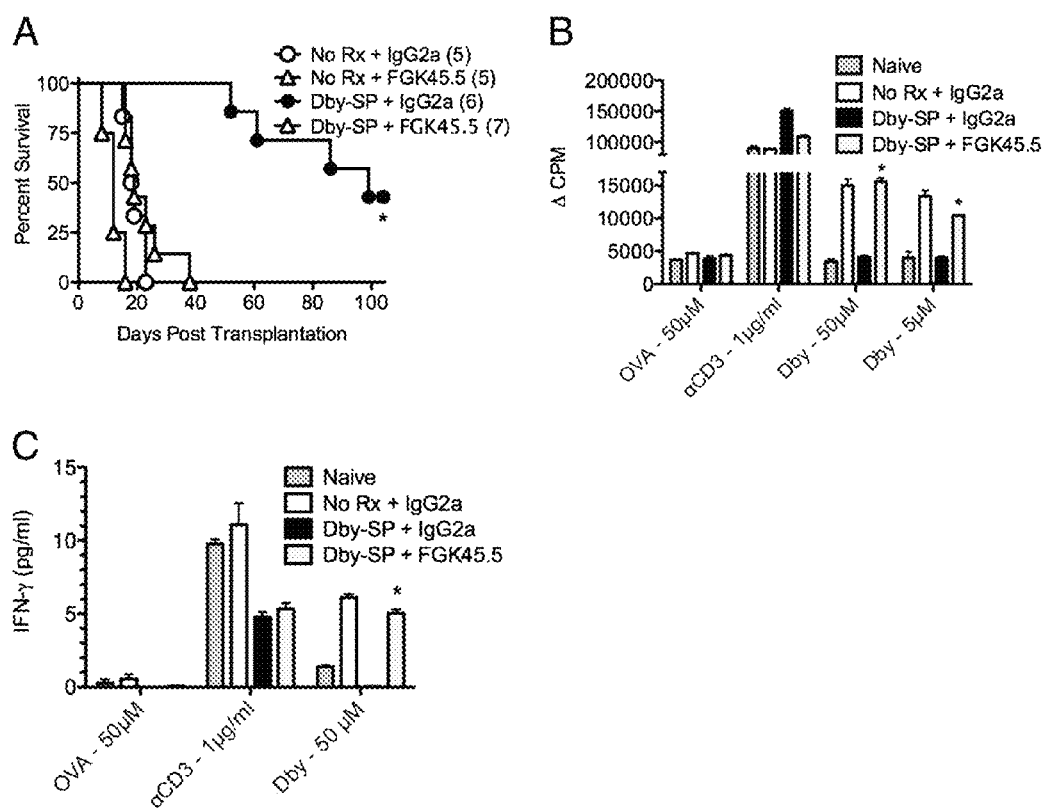
FIG. 11 shows Dby-SP-induced protection of Hya skin grafts is reversed by CD40 cross-linking.
Figure 12:
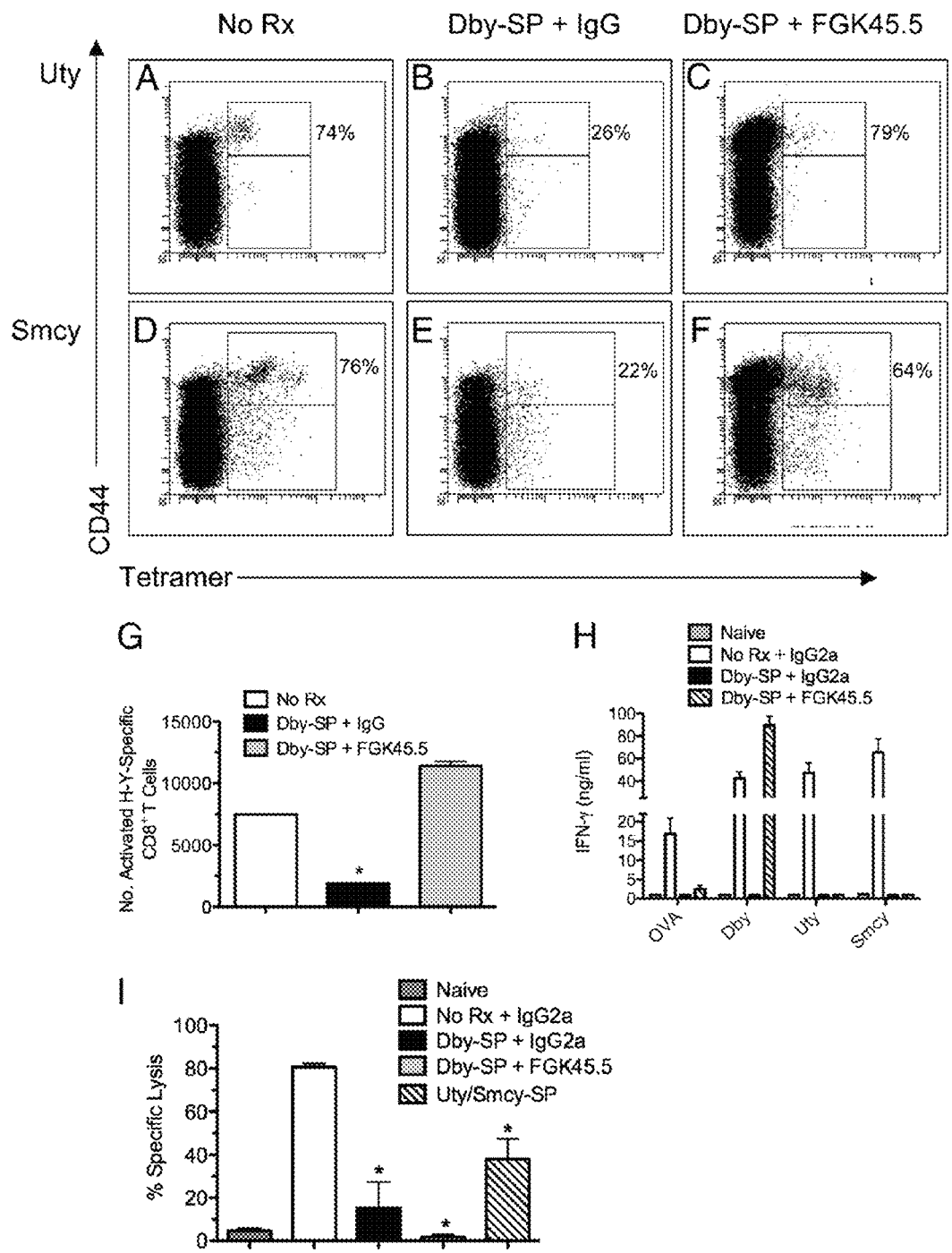
FIG. 12 shows FGK45.5-mediated reversal of Dby-SP-induced protection of Hya skin grafts is not associated with restoration of Hya-specific CD8 T cell IFN-γproduction or CTL activity. Untreated (No Rx) and Dby-SP-tolerized female B6 mice received male tail skin grafts on day 0. Twenty-four hours later, separate groups of Dby-SP-treated mice were injected i.p. with 100 μg IgG2a isotype control or with the agonistic anti-CD40 mAb, FGK45.5.

CD40 Stimulation Abrogates the Tolerogenic Effects of Dby-SP In Vivo and In Vitro To assess the functional significance of the observed defect in CD40L upregulation, the effect of administration of an agonist mAb specific for CD40 (clone FGK45.5) to Dby-SP-tolerized graft recipients was examined. This clone is known to bypass the requirement for CD4 help by stimulating the upregulation of costimulatory markers on APCs (Shepherd, D. M., N. I. Kerkvliet. 1999. *J. Immunol.* 163: 2470-2477). B6 females were tolerized with Dby-SPs on days −7 and 0, engrafted with male tail skin on day 0, and were treated i.p. with 100 μg FGK45.5 or control rat IgG2a 24 h after engraftment. Compared to Dby-SP-treated B6 females receiving isotype control Ab, which were significantly protected from the rejection of male tail skin grafts (median 78 d), Dby-SP-treated animals receiving FGK45.5 rejected male grafts (median 28 d) similarly to nontolerized controls (median 19 d) (SEE FIG. 11A), indicating that CD40 ligation overcomes the protection afforded by antigen-SP treatment. FGK45.5-induced in vivo stimulation of CD40 also reversed the suppression of Dby-specific in vitro proliferation (SEE FIG. 11B) and IFN-γ secretion (SEE FIG. 11C).

Cytometric analyses of Hya tetramer-positive $CD8^+$ cells demonstrate that FGK45.5 administration to Dby-SP-tolerized recipients, in comparison with control IgG2a treatment, resulted in a significant enhancement of the frequency and numbers of activated graft-specific Uty- and Smcy-specific T cells ($CD8^+$tetramer$^+CD44^+$), reaching levels similar those observed in nontolerized controls (SEE FIG. 12A-G). However, IFN-γ secretion in response to in vitro recall challenge with either the Uty or Smcy CD8 epitopes was not restored following FGK45.5 treatment of tolerized graft recipients (SEE FIG. 12H), nor was in vivo CTL function restored in tolerant recipients following CD40 ligation (SEE FIG. 12I). These data indicate that CD40 ligation overcomes functional antigen-SP-induced graft protection by reversing unresponsiveness in the Hya-specific $CD4^+$ compartment. Although anti-CD40 treatment resulted in recovery of control numbers of activated ($CD44^+$) Hya-specific $CD8^+$ T cells, the effector function of these cells as determined by IFN-γ production and lytic capacity was not restored.

Figure 13:
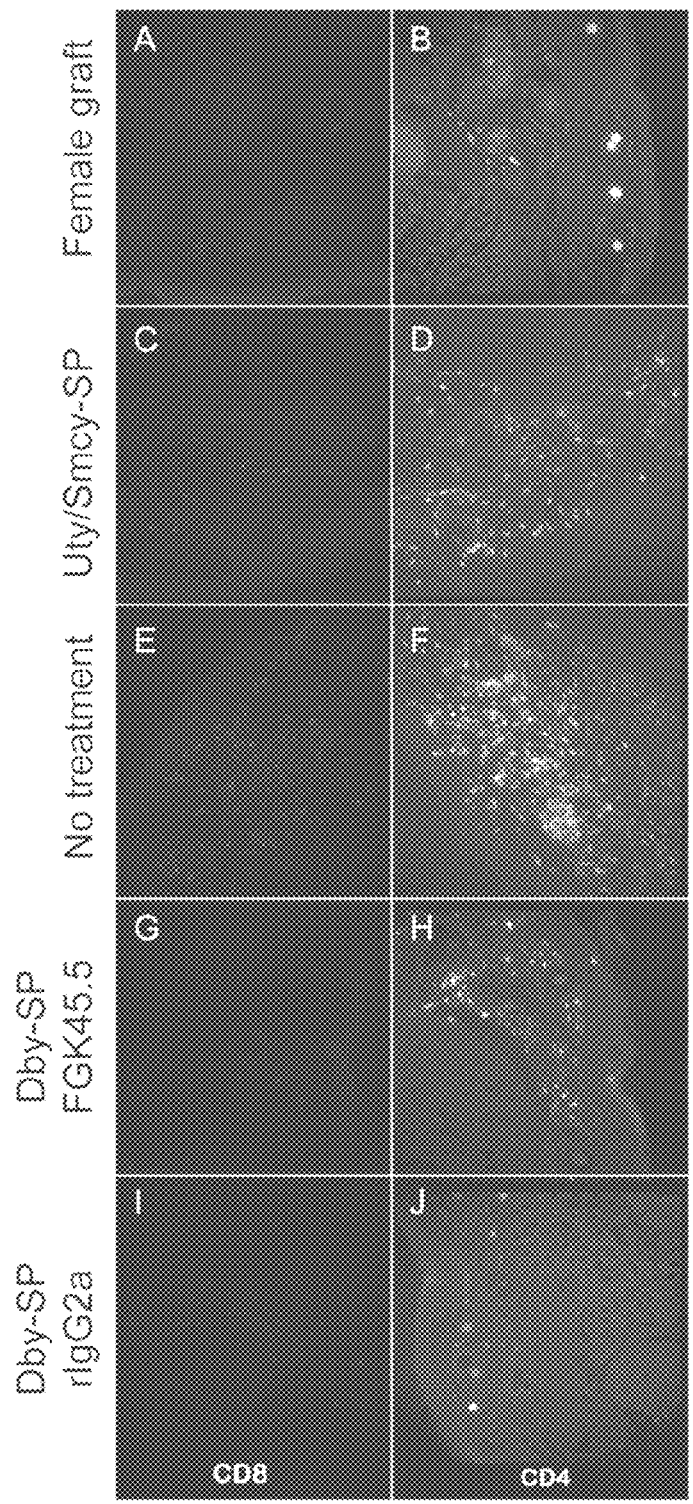
FIG. 13 shows reduced CD8 graft infiltrate does not correlate with graft survival.

Experiments conducted during development of embodiments of the present invention indicated that Hya-disparate graft destruction can take place despite an impaired CD8 response. This was confirmed by examining histological sections of engrafted skin for infiltrating $CD4^+$ and $CD8^+$ cells (SEE FIG. 13). Male grafts on nontreated rejecting controls contain significant $CD4^+$ and $CD8^+$ infiltrate, whereas grafts from Dby-SP-treated animals contain greatly reduced CD4 infiltrate and virtually no infiltrating $CD8^+$ T cells, consistent with their prolonged survival. Conversely, grafts from animals receiving Dby-SPs followed by an FGK45.5 treatment contained $CD4^+$ cells but virtually no $CD8^+$ cells. A similar observation was made in grafts from Uty/Smcy-treated animals, which were found to contain significant $CD4^+$ infiltrate but reduced $CD8^+$ infiltrate, indicating that FGK45.5 treatment restores the ability of $CD4^+$ but not $CD8^+$ T cells to infiltrate the grafts of Dby-SP-treated mice. These data indicate that Hya-disparate graft rejection can occur in the context of an impaired (following Uty/Smcy-SP treatment) or completely nonfunctioning (following Dby-SP and FGK45.5 treatment) CTL response.

Figure 14:
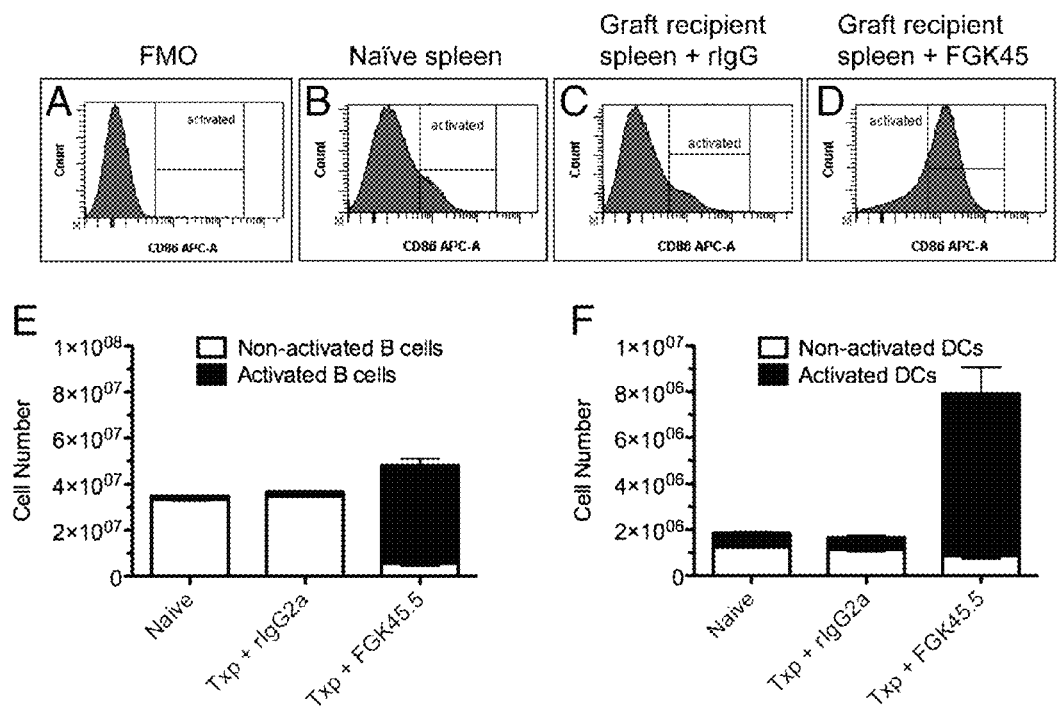
FIG. 14 shows FGK45.5 treatment results in increased numbers of activated B cells and DCs. B6 females were engrafted with skin from a CD45.1 congenic donor female. Twenty-four hours posttransplantation, recipient animals received 100 μg FGK45.5 or rat IgG2a via i.p. injection. Forty-eight hours after antibody treatment (and 72 h posttransplantation), spleens and lymph nodes were analyzed for the expression of the B7 family costimulatory molecule CD86 on various lineages of APCs.

The effects of FGK45.5 binding on the recipient APC populations were measured by cytometric analysis. Female B6 animals were transplanted with CD45.1 congenic skin 24 h prior to i.p. injection of FGK45.5 or control rat IgG. Seventy-two hours posttransplantation, spleens and lymph nodes were analyzed for APC activation, as determined by increased expression of the B7 family costimulatory molecule CD86. FGK45.5 treatment broadly activated APCs, as demonstrated by the large increase in $CD86^+$ cells (SEE FIG. 14D). Lineage phenotyping of the $CD86^+$ population revealed that the primary activated APC population was B cells (75-80% of the $CD86^+$ population, SEE FIG. 14E), although a significant expansion and activation of DCs was also observed (SEE FIG. 14F).

Alloantigenic Peptides Attached to Syngeneic Leukocytes Using ECDI Confer Dominant Antigen-Specific Transplant Protection Experiments conducted during development of embodiments of the present invention demonstrate that minor Hya alloantigenic peptides attached to syngeneic leukocytes using ECDI confer dominant antigen-specific transplant protection dependent on alteration of CD40/CD154 signaling. Induction of graft protection was dependent on the administration of cells coupled with the dominant CD4 epitope (Dby) but not CD8 epitopes (Uty and Smcy) of male antigen. Experiments conducted during development of embodiments of the present invention demonstrated that Dby-coupled female splenocytes conferred significant protection to male skin grafts (SEE FIG. 7). Although protection was observed using an equivalent number of ECDI-fixed male splenocytes (median survival 39 d), the protection was inferior to that conferred by Dby-SPs.

Treatment with Dby-SPs significantly diminished DTH responses to Dby in vivo and reduced Dby-specific in vitro recall responses as assessed by proliferation and IFN-γ production, indicating profound unresponsiveness in the CD4 compartment. Further, Dby-SP-tolerized mice failed to develop CTLs specific for the immunodominant Hya CD8 T cell epitopes. Experiments conducted during development of embodiments of the present invention indicate that antigen-SP therapy can be successfully used to specifically control the rejection of mismatched tissue grafts with the proviso that the epitopes are known. Importantly, both CD4 and CD8 responses are diminished in the absence of broad-scale immunosuppressive agents, and CD40-CD154 interactions are safely inhibited. Complementing the observed defect in CD154 expression with anti-CD40 treatment restored graft rejection through CD4 reactivation but not through CD8 activation.

FGK45 treatment of Dby-SP-treated mice restored normal levels of graft rejection as well as graft infiltration, proliferation, and IFN-γ responses in the CD4 compartment but not infiltration, lysis, or IFN-γ responses in the CD8 compartment. These findings are in agreement with work performed using FGK45, which collectively suggests that FGK45 effects on tumor and graft destruction are mediated primarily through CD4 T cells. CTL responses against P815 tumor cells are not initiated in $CD154^{-/-}$ mice, and neither FGK45.5 treatment nor the use of B7 overexpressing P815 cells restored CTL function, indicating that increased costimulation alone is insufficient for CTL priming in the absence of CD4 help/CD154 (Shepherd & Kerkvliet. 1999. *J. Immunol.* 163: 2470-2477; herein incorporated by reference in its entirety). FGK45 treatment only partially restores CTL function and allograft destruction in $CD4^{-/-}$ mice. Experiments conducted during development of the present invention indicate that, bolstered by FGK45 treatment, sufficient CD4 activation occurs to prime protective antitumor CTL responses prior to the depletion of Th cells.

Experiments conducted during development of embodiments of the present invention demonstrated that antigen-SP encounter induces a defect in CD154 expression in the targeted T cell and that this defect is crucial to the protection of Hya-disparate grafts. Diminished proliferative responses of T cells from Dby-SP-treated male graft recipients in response to Dby rechallenge could be rescued by the addition of exogenous IL-2 (SEE FIG. 7C). IL-2 is a critical factor in CD4 priming of CD8 responses. Although grafts were retained in Uty-iDC recipients, Uty-specific CD8$^+$ T cells displayed an activated phenotype and secreted IFN-γ in recall assays. Experiments conducted during development of embodiments of the present invention indicate that Uty-iDCs may have induced antigen-specific CD8 responses but because the activation occurred in the absence of CD4-derived IL-2, a productive memory response was not induced. In some embodiments, using antigen-SPs, the route of administration is a critical parameter, because s.c. injection stimulates DTH responses, whereas i.v. injection induces tolerance (Miller, S et al. 1979. *J. Exp. Med.* 149: 758-773.; herein incorporated by reference in its entirety).

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for cell or allograft transplantation comprising:
   a) administering a first type of cells to a recipient prior to step b), wherein said first type of cells are from a donor and are ECDI-treated cells;
   b) administering a second type of cells or an allograft to said recipient, wherein said second type of cells and said allograft are from said donor; and
   c) administering said first type of cells to said recipient); wherein said administering in step c) is performed 1-96 hours after step b).

2. The method of claim 1, wherein said administering in step c) is performed 12-36 hours after step b).

3. The method of claim 1, wherein said administering in step a) is performed 1-14 days prior to step b).

4. The method of claim 1, wherein said administering in step a) is performed 4-10 days prior to step b).

5. The method of claim 1, wherein said first type of cells comprise leukocytes.

6. The method of claim 1, wherein said first type of cells comprise splenocytes.

7. The method of claim 1, wherein said second type of cells comprise parenchymal cells from an organ.

8. The method of claim 1, wherein said second type of cells comprise islet cells.

9. The method of claim 1, wherein said allograft comprises at least part of an organ selected from the group consisting of: kidney, pancreas, heart, liver, large intestine, small intestine, lung, and stomach.

10. The method of claim 1, wherein said administering in steps a) and c) induces donor-specific tolerance to said second type of cells or said allograft in said recipient.

11. The method of claim 10, wherein said donor-specific tolerance to said second type of cells or said allograft lasts for at least 50 days in said recipient in the absence of an additional immunosuppressive regime.

12. The method of claim 10, wherein said recipient has not received any additional immunosuppressive agents for at least 50 days from step b), and said second type of cells and/or said allograft are not rejected for said at least 50 days.

13. The method of claim 1, wherein said ECDI-treated cells comprise cells which were contacted with ECDI in the presence of one or more antigens and/or epitopes.

* * * * *